(12) United States Patent
Olsen et al.

(10) Patent No.: US 11,939,408 B2
(45) Date of Patent: Mar. 26, 2024

(54) HYALURONIC ACID DERIVATIVES

(71) Applicant: Massachusetts Institute of Technology, Cambridge, MA (US)

(72) Inventors: Bradley David Olsen, Arlington, MA (US); Allie Obermeyer, New York, NY (US); Sieun Kim Barnes, Melrose, MA (US); Yun Jung Yang, Incheon (KR)

(73) Assignee: Massachusetts Institute of Technology, Cambridge, MA (US)

( * ) Notice: Subject to any disclaimer, the term of this patent is extended or adjusted under 35 U.S.C. 154(b) by 96 days.

(21) Appl. No.: 17/126,700

(22) Filed: Dec. 18, 2020

(65) Prior Publication Data

US 2021/0189018 A1 Jun. 24, 2021

Related U.S. Application Data

(60) Provisional application No. 62/951,438, filed on Dec. 20, 2019.

(51) Int. Cl.
| | |
|---|---|
| *C08B 37/08* | (2006.01) |
| *A61K 8/73* | (2006.01) |
| *A61Q 19/08* | (2006.01) |

(52) U.S. Cl.
CPC .......... *C08B 37/0072* (2013.01); *A61K 8/735* (2013.01); *A61Q 19/08* (2013.01)

(58) Field of Classification Search
None
See application file for complete search history.

(56) References Cited

U.S. PATENT DOCUMENTS

2018/0036220 A1* 2/2018 Bouchemal .......... A61K 31/728

FOREIGN PATENT DOCUMENTS

| EP | 3241852 A1 | 11/2017 | |
|---|---|---|---|
| EP | 3241852 B1 * | 10/2018 | ........... A61K 31/704 |

OTHER PUBLICATIONS

Kong et al., Design and investigation of nanoemulsified carrier based on amphiphile-modified hyaluronic acid. Polymers. 2011;83(2):462-469. https://doi.org/10.1016/j.carbpol.2010.08.001.
Mero et al., Hyaluronic Acid Bioconjugates for the Delivery of Bioactive Molecules. Polymers 2014, 6, 346-369. https://doi.org/10.3390/polym6020346.

(Continued)

*Primary Examiner* — Kyung S Chang
(74) *Attorney, Agent, or Firm* — Wolf, Greenfield & Sacks, P.C.

(57) ABSTRACT

Skin hydration is necessary to maintain the epidermal barrier, minimize adverse environmental influences, and reduce cell stress. Provided herein are compounds, such as compounds of Formula (I), and pharmaceutically and cosmetically acceptable salts thereof, and compositions, methods, and uses that may be used for skin hydration. Also reported herein is a scalable method for synthesizing compounds of Formula (I). The compounds provided herein are responsible for improved skin penetration and/or retention and are therefore useful for the treatment and/or prevention of various diseases, disorders, or conditions to protect human skin.

13 Claims, 6 Drawing Sheets

(56) References Cited

OTHER PUBLICATIONS

Yue et al., Hyaluronic acid modified nanostructured lipid carriers for transdermal bupivacaine delivery: In vitro and in vivo anesthesia evaluation. Biomed Pharmacother. Feb. 2018;98:813-820. doi: 10.1016/j.biopha.2017.12.103. Epub Jan. 5, 2018. PMID: 29571251.
Abd et al., Skin models for the testing of transdermal drugs. Clin Pharmacol. Oct. 19, 2016;8:163-176.
Andrews et al., Recovery of skin barrier after stratum corneum removal by microdermabrasion. AAPS PharmSciTech. Dec. 2011;12(4):1393-400. doi: 10.1208/s12249-011-9715-x. Epub Oct. 19, 2011.
Baumann, Skin ageing and its treatment. J Pathol. Jan. 2007;211(2):241-51.
Becker et al., Final Report of the Safety Assessment of Hyaluronic Acid, Potassium Hyaluronate, and Sodium Hyaluronate. Int. J. Toxicol. 2009, 28 (4 Suppl), 5-67.
Boer et al., Structural and biophysical characteristics of human skin in maintaining proper epidermal barrier function. Postepy Dermatol Alergol. Feb. 2016;33(1):1-5. doi: 10.5114/pdia.2015.48037. Epub Feb. 29, 2016.
Chen et al., Topical delivery of hyaluronic acid into skin using SPACE-peptide carriers. J Control Release. Jan. 10, 2014;173:67-74. doi: 10.1016/j.jconrel.2013.10.007. Epub Oct. 12, 2013.
Chiummariello et al., Il trattamento topico di ulcere da pressione con aminoacidi e acido ialuronico. Caso clinico [Aminoacids and hyaluronic acid in topical treatment of bedsores. Clinical report]. G Chir. May 2010;31(5):251-5. English abstract.
Dunetz et al., Large-scale applications of amide coupling reagents for the synthesis of pharmaceuticals. Org Process Res Dev. 2016; 20(2): 140-77.
Essendoubi et al., Human skin penetration of hyaluronic acid of different molecular weights as probed by Raman spectroscopy. Skin Res Technol. Feb. 2016;22(1):55-62. doi: 10.1111/srt.12228. Epub Apr. 16, 2015.
Fallacara et al., Hyaluronic Acid in the Third Millennium. Polymers (Basel). Jun. 25, 2018;10(7):701.
Farage et al., Characteristics of the Aging Skin. Adv Wound Care (New Rochelle). Feb. 2013;2(1):5-10.
Ganesh et al., Hyaluronic acid based self-assembling nanosystems for CD44 target mediated siRNA delivery to solid tumors. Biomaterials. Apr. 2013;34(13):3489-502. doi: 10.1016/j.biomaterials.2013.01.077. Epub Feb. 11, 2013.
Jiang et al., Hyaluronan as an immune regulator in human diseases. Physiol Rev. Jan. 2011;91(1):221-64.
Kezutyte et al., Studying the penetration of fatty acids into human skin by ex vivo TOF-SIMS imaging. Biointerphases. Dec. 2013;8(1):3. doi: 10.1186/1559-4106-8-3. Epub Feb. 6, 2013.
Kim et al., Skin permeation enhancement of diclofenac by fatty acids. Drug Deliv. Aug. 2008; 15(6):373-9.
Koniev et al., Developments and recent advancements in the field of endogenous amino acid selective bond forming reactions for bioconjugation. Chem Soc Rev. Aug. 7, 2015;44(15):5743. doi: 10.1039/c5cs90060c. Erratum for: Chem Soc Rev. Aug. 7, 2015;44(15):5495-551.
Kuehl et al., Hyaluronic Acid Molecular Weight Determines Lung Clearance and Biodistribution after Instillation. Mol Pharm. Jun. 6, 2016;13(6):1904-14. doi: 10.1021/acs.molpharmaceut.6b00069. Epub May 24, 2016.
Lee et al., Hyaluronic acid-paclitaxel conjugate micelles: synthesis, characterization, and antitumor activity. Bioconjug Chem. Jun. 2008;19(6):1319-25. doi: 10.1021/bc8000485. Epub May 16, 2008.
Lin et al., Anti-Inflammatory and Skin Barrier Repair Effects of Topical Application of Some Plant Oils. Int J Mol Sci. Dec. 27, 2017;19(1):70.
Longinotti, The use of hyaluronic acid based dressings to treat burns: A review. Burns Trauma. Oct. 25, 2014;2(4):162-8.
Lopes, Overcoming the cutaneous barrier with microemulsions. Pharmaceutics. Feb. 28, 2014;6(1):52-77.
Martins et al., Design of novel BSA/hyaluronic acid nanodispersions for transdermal pharma purposes. Mol Pharm. May 5, 2014;11(5):1479-88. doi: 10.1021/mp400657g. Epub Apr. 1, 2014.
Mckay et al., Click chemistry in complex mixtures: bioorthogonal bioconjugation. Chem Biol. Sep. 18, 2014;21(9):1075-101.
Mero et al., Hyaluronic acid bioconjugates for the delivery of bioactive molecules. Polymers. 2014; 6(2): 346-69.
Nakama et al., Temperature- and pH-controlled hydrogelation of poly(ethylene glycol)-grafted hyaluronic acid by inclusion complexation with α-cyclodextrin. Polymer J. 2004; 36: 338-44.
Pappas, Epidermal surface lipids. Dermatoendocrinol. Mar. 2009;1(2):72-6.
Sano et al., Age-related changes in cyclic phosphatidic acid-induced hyaluronic acid synthesis in human fibroblasts. Hum Cell. Jan. 2018;31(1):72-77. doi: 10.1007/s13577-017-0185-7. Epub Oct. 23, 2017.
Scheller et al., The pro- and anti-inflammatory properties of the cytokine interleukin-6. Biochim Biophys Acta. May 2011;1813(5):878-88. doi: 10.1016/j.bbamcr.2011.01.034. Epub Feb. 4, 2011.
Schiraldi et al., Biotechnological Production and Application of Hyaluronan. Chapter 2. Biopolymers 2010. 27 pages.
Shokri et al., Effects of skin penetration enhancers in topical antiaging products containing α-hydroxyacids and hyaluronic acid. Avicenna J Med Biochem. 2014; 2(2): 18611.
Stephanopoulos et al., Choosing an effective protein bioconjugation strategy. Nat Chem Biol. Nov. 15, 2011;7(12):876-84.
Tokudome et al., A new strategy for the passive skin delivery of nanoparticulate, high molecular weight hyaluronic acid prepared by a polyion complex method. Sci Rep. Feb. 5, 2018;8(1):2336.
Uchiyama et al., Free fatty acids chain length distribution affects the permeability of skin lipid model membranes. Biochim Biophys Acta. Sep. 2016;1858(9):2050-2059. doi: 10.1016/j.bbamem.2016.06.001. Epub Jun. 7, 2016.

* cited by examiner

HYALURONIC ACID DERIVATIVES

CROSS REFERENCE TO RELATED APPLICATIONS

The present application claims priority under 35 U.S.C. § 119(e) to U.S. Provisional Application, U.S. Ser. No. 62/951,438, filed on Dec. 20, 2019, which is incorporated herein by reference in its entirety.

BACKGROUND

Human skin aging is due to progressive structural and functional degeneration by complex and dynamic biological processes.[1,2] One of the common causes of skin aging is the loss of skin moisture.[3] To slow down or stop the aging process, hydration of the skin is essential to maintaining the epidermal barrier, making a suitable environment for the cells of the epidermis and dermis.[4] Providing optimal hydration and moisture to skin reduces adverse environmental influences and cell stress. Hence, the process of hydrating living layers in skin, shifting and retaining water into cells, is essential. Consequently, there is a large market for skin moisturizing products.

One very common ingredient in these and other personal care and medical products is hyaluronic acid (HA). HA is also a considerable component of the human body. For example, an adult body of 70 kg contains approximately 15 g HA.[5] Among the total HA, 50% is found in the skin, including the dermis and epidermis.[6,7] HA plays a role in wound healing and regulation of skin cells as a key molecule in the skin.[3,8] This is due to the fact that HA also engages a particular healing process in early inflammation and enhances cellular infiltration.[9,10] As such, this naturally produced material has a variety of uses. HA has been used as a treatment for relieving burns[11], bed sores[12], wounds[13], and skin ulcers[14] when applied topically. In addition, HA has been used as a booster of skin hydration and skin elasticity in the cosmetic industry, where it is a common ingredient in products from many companies,[5,15] because it binds and retains water molecules. In aging skin, HA completely disappears from the dermis, resulting in loss of skin moisture and elasticity in the skin.[16,17] Therefore, providing HA in both pharmaceutical and cosmetic formulations is crucial to protect human skin.[18]

However, the physiological function of the stratum corneum is as protective barrier prevents the permeation of hydrophilic molecules and large molecules (>500 Da) into deeper skin layers.[19] Therefore, the poor skin permeability of high molecular weight HA is a significant challenge. While low molecular weight HA shows better permeability, it is poorly retained in the skin.[20,21] In addition, there are several reports that HA has a short lifetime of approximately 3 to 5 mins in circulating blood and less than 24 hours in animal skin models via hydrolyzing the hexosaminidic β (1-4) linkages between N-acetyl-D-glucosamine and D-glucuronic acid in the HA backbone.[3,22,23] Therefore, developing HA with enhanced skin permeability as well as longer skin retention offers enhanced infusion of skin layers with water to maintain skin hydration.

SUMMARY OF THE INVENTION

The present disclosure provides compounds (e.g., compounds of Formula (I)), and pharmaceutically and cosmetically acceptable salts thereof, pharmaceutical and cosmetic compositions, and kits thereof. In certain embodiments, the compounds provided herein exhibit improved skin retention and/or penetration.

The present disclosure also provides methods of making the compounds provided herein.

The present disclosure also provides methods of using the compounds and compositions provided herein, e.g., for treating and/or preventing a disease, disorder, or condition in a subject.

In one aspect, the disclosure provides compounds of Formula (I):

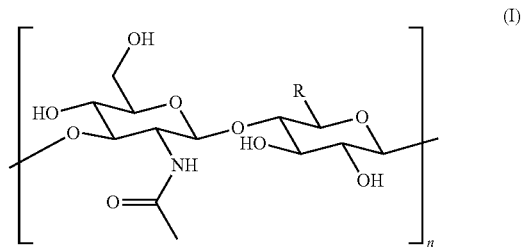

and pharmaceutically and cosmetically acceptable salts thereof, wherein the variables R and n recited in Formula (I) are as described herein.

In some embodiments, the disclosure provides compounds of Formula (I), or pharmaceutically or cosmetically acceptable salts thereof, wherein R is of formula (II):

wherein the variables $R^2$ and L recited in Formula (II) are as described herein.

In certain embodiments of Formula (I), or a pharmaceutically or cosmetically acceptable salt thereof:
n is an integer from 5-50;
each R is independently —CO$_2$H, or a group of Formula (II):

wherein L is

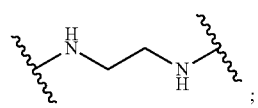 [SMILES: *NCCN*]

and
$R_2$ is a fatty acid residue of the formula —C(O)R$_3$, wherein $R_3$ is $C_{9-19}$ unsubstituted alkyl;
provided that at least 1% of R groups comprise a group of Formula (II).

In another aspect, the present disclosure provides compositions comprising an effective amount of a compound provided herein (e.g., a compound of Formula (I)), or a pharmaceutically or cosmetically acceptable salt thereof, and optionally a pharmaceutically acceptable carrier or excipient.

In certain embodiments, the composition is a pharmaceutical composition. In some embodiments, the composition is a cosmetic composition. In some embodiments, the composition comprises an additional pharmaceutical agent. In certain embodiments, the composition comprises an additional cosmetic agent. In some embodiments, the composition is characterized as having increased skin penetration relative to unmodified hyaluronic acid of Formula (Ia):

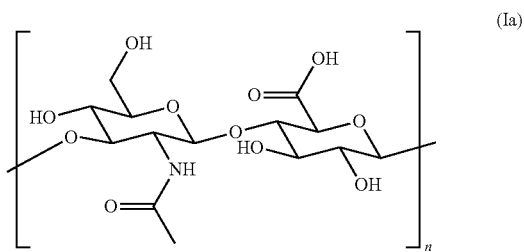

(Ia)

or a salt thereof, wherein n is an integer from 1-20,000. In certain embodiments, the composition is characterized as having increased skin retention relative to unmodified hyaluronic acid of Formula (Ia), or a salt thereof.

In another aspect, the present disclosure provides methods of making a compound of Formula (I), or a pharmaceutically or cosmetically acceptable salt thereof, the method comprising:

a) Providing a solution of unmodified hyaluronic acid of Formula (Ia):

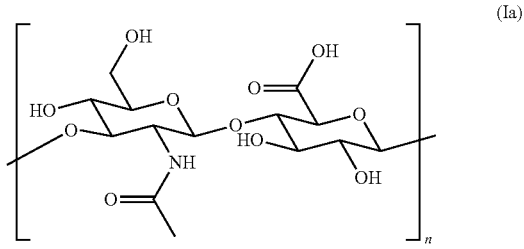

(Ia)

or a salt thereof, wherein n is an integer from 1-20,000;

b) Contacting the solution with a diaminoalkyl compound under suitable conditions to obtain amine-functionalized HA, or a salt thereof;

c) Reacting the amine-functionalized HA or salt thereof with a compound comprising a hydrophobic moiety, to obtain the compound of Formula (I), or pharmaceutically or cosmetically acceptable salt thereof.

In yet another aspect, the present disclosure provides methods of treating and/or preventing a disease, disorder, or condition in a subject comprising administering to the subject an effective amount of a compound provided herein (e.g., a compound of Formula (I)), or a pharmaceutically or cosmetically acceptable salt thereof, or a pharmaceutic or cosmetic composition thereof.

In certain embodiments, the disease, disorder, or condition is skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles.

The details of certain embodiments of the invention are set forth in the Detailed Description of Certain Embodiments, as described below. Other features, objects, and advantages of the invention will be apparent from the Definitions, Examples, Figures, and Claims. It should be understood that the aspects described herein are not limited to specific embodiments, methods, or configurations, and as such can, of course, vary. It is also to be understood that the terminology used herein is for the purpose of describing particular aspects only and, unless specifically defined herein, is not intended to be limiting.

BRIEF DESCRIPTION OF THE DRAWINGS

The accompanying drawings, which are incorporated in and constitute a part of this specification, illustrate several embodiments of the invention and together with the description, provide non-limiting examples of the invention.

FIG. 1A shows the reaction for the synthesis of NHS-lipid. FIG. 1B shows the synthesis of HA-lipid conjugation with a two-step, ethylene diamine and NHS-lipid. FIG. 1C shows labeling HA-lipid with FITC for skin penetration test.

FIG. 3A shows the $^1H$ NMR spectrum of unmodified HA. FIG. 3B shows the $^1H$ NMR spectrum of HA-lipid conjugation.

DEFINITIONS

Chemical Definitions

Figures 1A, 1B, 1C:
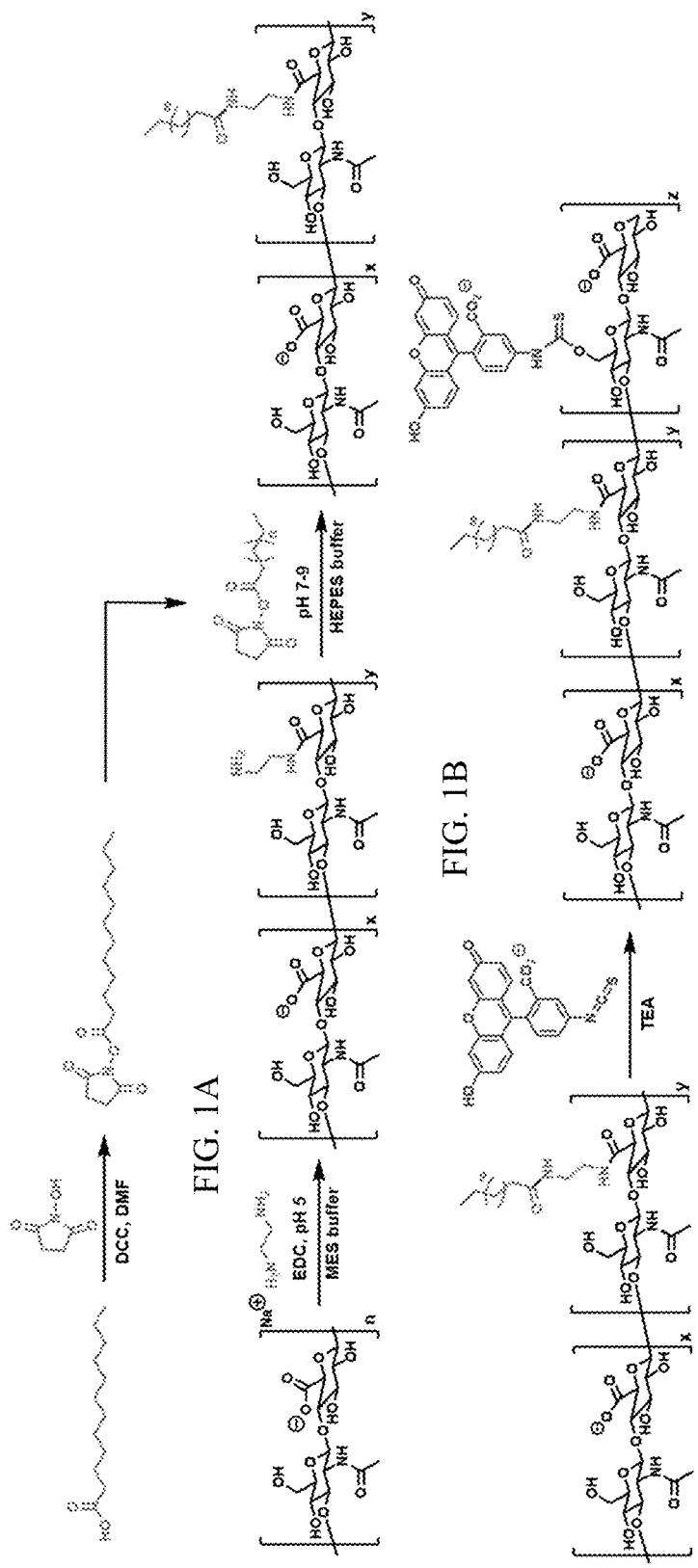
FIGS. 1A-1C show chemical reactions.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry*, 7$^{th}$ Edition, John Wiley & Sons, Inc., New York, 2013; Richard C. Larock, *Comprehensive Organic Transformations*, John Wiley & Sons, Inc., New York, 2018; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

When a range of values is listed, it is intended to encompass each value and sub-range within the range. A range is inclusive of the values at the two ends of the range unless otherwise provided. For example "$C_{1-6}$ alkyl" encompasses, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_1$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 20 carbon atoms ("$C_{1-20}$ haloalkyl"). In some embodiments, the haloalkyl moiety has 1 to 10 carbon atoms ("$C_{1-10}$ haloalkyl"). In some embodiments, the haloalkyl moiety has 1 to 9 carbon atoms ("$C_{1-9}$ haloalkyl"). In some embodiments, the haloalkyl moiety has 1 to 8 carbon atoms ("$C_{1-8}$ haloalkyl"). In some embodiments, the haloalkyl moiety has 1 to 7 carbon atoms ("$C_{1-7}$ haloalkyl"), In some embodiments, the haloalkyl moiety has 1 to 6 carbon atoms ("$C_{1-6}$ haloalkyl"). In some embodiments, the haloalkyl moiety has 1 to 5 carbon atoms ("$C_{1-5}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are independently replaced with fluoro to provide a "perfluoroalkyl" group. In some embodiments, all of the haloalkyl hydrogen atoms are independently replaced with chloro to provide a "perchloroalkyl" group. Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("heteroC$_{1-20}$ alkyl"). In certain embodiments, a heteroalkyl group refers to a saturated group having from 1 to 12 carbon atoms and 1 or more heteroatoms within the parent chain ("heteroC$_{1-12}$ alkyl"). In some embodiments, a heteroalkyl group is a saturated group having 1 to 11 carbon atoms and 1 or more heteroatoms within the parent chain ("heteroC$_{1-11}$ alkyl"). In some embodiments, a heteroalkyl group is a saturated group having 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-12}$ alkyl. In certain embodiments, the heteroalkyl group is a substituted heteroC$_{1-12}$ alkyl.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("C$_{1-20}$ alkenyl"). In some embodiments, an alkenyl group has 1 to 12 carbon atoms ("C$_{1-12}$ alkenyl"). In some embodiments, an alkenyl group has 1 to 11 carbon atoms ("C$_{1-11}$ alkenyl"). In some embodiments, an alkenyl group has 1 to 10 carbon atoms ("C$_{1-10}$ alkenyl"). In some embodiments, an alkenyl group has 1 to 9 carbon atoms ("C$_{1-9}$ alkenyl"). In some embodiments, an alkenyl group has 1 to 8 carbon atoms ("C$_{1-8}$ alkenyl"). In some embodiments, an alkenyl group has 1 to 7 carbon atoms ("C$_{1-7}$ alkenyl"). In some embodiments, an alkenyl group has 1 to 6 carbon atoms ("C$_{1-6}$ alkenyl"). In some embodiments, an alkenyl group has 1 to 5 carbon atoms ("C$_{1-5}$ alkenyl"). In some embodiments, an alkenyl group has 1 to 4 carbon atoms ("C$_{1-4}$ alkenyl"). In some embodiments, an alkenyl group has 1 to 3 carbon atoms ("C$_{1-3}$ alkenyl"). In some embodiments, an alkenyl group has 1 to 2 carbon atoms ("C$_{1-2}$ alkenyl"). In some embodiments, an alkenyl group has 1 carbon atom ("C$_1$ alkenyl"). The one or more carbon-carbon double bonds can be internal (such as in 2-butenyl) or terminal (such as in 1-butenyl). Examples of C$_{1-4}$ alkenyl groups include methylidenyl (C$_1$), ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{1-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{1-20}$ alkenyl. In certain embodiments, the alkenyl group is a substituted C$_{1-20}$ alkenyl. In an alkenyl group, a C=C double bond for which the stereochemistry is not specified (e.g., —CH=CHCH$_3$ or

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 1 to 20 carbon atoms, at least one double bond, and 1 or more heteroatoms within the parent chain ("heteroC$_{1-20}$ alkenyl"). In certain embodiments, a heteroalkenyl group refers to a group having from 1 to 12 carbon atoms, at least one double bond, and 1 or more heteroatoms within the parent chain ("heteroC$_{1-12}$ alkenyl"). In certain embodiments, a heteroalkenyl group refers to a group having from 1 to 11 carbon atoms, at least one double bond, and 1 or more heteroatoms within the parent chain ("heteroC$_{1-11}$ alkenyl"). In certain embodiments, a heteroalkenyl group refers to a group having from 1 to 10 carbon atoms, at least one double bond, and 1 or more heteroatoms within the parent chain ("heteroC$_{1-10}$ alkenyl"). In some embodiments, a heteroalkenyl group has 1 to 9 carbon atoms at least one double bond, and 1 or more heteroatoms within the parent chain ("heteroC$_{1-9}$ alkenyl"). In some embodiments, a heteroalkenyl group has 1 to 8 carbon atoms, at least one double bond, and 1 or more heteroatoms within the parent chain ("heteroC$_{1-8}$ alkenyl"). In some embodiments, a heteroalkenyl group has 1 to 7 carbon atoms, at least one double bond, and 1 or more heteroatoms within the parent chain ("heteroC$_{1-7}$ alkenyl"). In some embodiments, a heteroalkenyl group has 1 to 6 carbon atoms, at least one double bond, and 1 or more heteroatoms within the parent chain ("heteroC$_{1-6}$ alkenyl"). In some embodiments, a heteroalkenyl group has 1 to 5 carbon atoms, at least one double bond, and 1 or 2 heteroatoms within the parent chain ("heteroC$_{1-5}$ alkenyl"). In some embodiments, a heteroalkenyl group has 1 to 4 carbon atoms, at least one double bond, and 1 or 2 heteroatoms within the parent chain ("heteroC$_{1-4}$ alkenyl"). In some embodiments, a heteroalkenyl group has 1 to 3 carbon atoms, at least one double bond, and 1 heteroatom within the parent chain ("heteroC$_{1-3}$ alkenyl"). In some embodiments, a heteroalkenyl group has 1 to 2 carbon atoms, at least one double bond, and 1 heteroatom within the parent chain ("heteroC$_{1-2}$ alkenyl"). In some embodiments, a heteroalkenyl group has 1 to 6 carbon atoms, at least one double bond, and 1 or 2 heteroatoms within the parent chain ("heteroC$_{1-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{1-20}$ alkenyl. In certain embodiments, the heteroalkenyl group is a substituted heteroC$_{1-20}$ alkenyl.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("C$_{1-20}$ alkynyl"). In some embodiments, an alkynyl group has 1 to 10 carbon atoms ("C$_{1-10}$ alkynyl"). In some embodiments, an alkynyl group has 1 to 9 carbon atoms ("C$_{1-9}$ alkynyl"). In some embodiments, an alkynyl group has 1 to 8 carbon atoms ("C$_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("hetero$C_{1-20}$ alkynyl"). In certain embodiments, a heteroalkynyl group refers to a group having from 1 to 10 carbon atoms, at least one triple bond, and 1 or more heteroatoms within the parent chain ("hetero$C_{1-10}$ alkynyl"). In some embodiments, a heteroalkynyl group has 1 to 9 carbon atoms, at least one triple bond, and 1 or more heteroatoms within the parent chain ("hetero$C_{1-9}$ alkynyl"). In some embodiments, a heteroalkynyl group has 1 to 8 carbon atoms, at least one triple bond, and 1 or more heteroatoms within the parent chain ("hetero$C_{1-8}$ alkynyl"). In some embodiments, a heteroalkynyl group has 1 to 7 carbon atoms, at least one triple bond, and 1 or more heteroatoms within the parent chain ("hetero$C_{1-7}$ alkynyl"). In some embodiments, a heteroalkynyl group has 1 to 6 carbon atoms, at least one triple bond, and 1 or more heteroatoms within the parent chain ("hetero$C_{1-6}$ alkynyl"). In some embodiments, a heteroalkynyl group has 1 to 5 carbon atoms, at least one triple bond, and 1 or 2 heteroatoms within the parent chain ("hetero$C_{1-5}$ alkynyl"). In some embodiments, a heteroalkynyl group has 1 to 4 carbon atoms, at least one triple bond, and for 2 heteroatoms within the parent chain ("hetero$C_{1-4}$ alkynyl"). In some embodiments, a heteroalkynyl group has 1 to 3 carbon atoms, at least one triple bond, and 1 heteroatom within the parent chain ("hetero$C_{1-3}$ alkynyl"). In some embodiments, a heteroalkynyl group has 1 to 2 carbon atoms, at least one triple bond, and 1 heteroatom within the parent chain ("hetero$C_{1-2}$ alkynyl"). In some embodiments, a heteroalkynyl group has 1 to 6 carbon atoms, at least one triple bond, and 1 or 2 heteroatoms within the parent chain ("hetero$C_{1-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{1-20}$ alkynyl. In certain embodiments, the heteroalkynyl group is a substituted hetero$C_{1-20}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{3-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. Exemplary $C_{3-8}$ carbocyclyl groups include the aforementioned $C_{3-10}$ carbocyclyl groups as well as cycloundecyl ($C_{11}$), spiro[5.5]undecanyl ($C_{11}$), cyclododecyl ($C_{12}$), cyclododecenyl ($C_{12}$), cyclotridecane ($C_{13}$), cyclotetradecane ($C_{14}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 r electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, e.g., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which is substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

Exemplary carbon atom substituents include halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O) R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O) NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O) (R$^{aa}$)$_2$, —P(=O)(OR$^{cc}$)$_2$, —OP(=O)(R$^{aa}$)$_2$, —OP(=O) (OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P (=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP (R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-20}$ alkenyl, heteroC$_{1-20}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C (=O)R$^{aa}$, =NNR$^{bb}$C(=O)OR$^{aa}$, =NNR$^{bb}$ S(=O)$_2$R$^{aa}$, =NR$^{bb}$, or =NOR$^{cc}$;

wherein:

each instance of R$^{aa}$ is, independently, selected from C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-20}$ alkenyl, heteroC$_{1-20}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$) N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-20}$ alkenyl, heteroC$_{1-20}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-20}$ alkyl, C$_{1-20}$ perhaloalkyl, C$_{1-20}$ alkenyl, C$_{1-20}$ alkynyl, heteroC$_{1-20}$ alkyl, heteroC$_{1-20}$ alkenyl, heteroC$_{1-20}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$ X$^-$, —N(OR$^{cc}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N (R$^{ff}$)$_2$, —C(=NR$^{ff}$) OR$^{ee}$, —OC(=NR$^{ff}$)R$^{ee}$, —OC (=NR$^{ff}$)OR$^{ee}$, —C(=NR$^{ff}$)N(R$^{ff}$)$_2$, —OC(=NR$^{ff}$)N (R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N (R$^{ff}$)$_2$, —C(=O)SR$^{ee}$, —C(=S)SR$^{ee}$, —S C(=S) SR$^{ee}$, —P(=O)(OR$^{ee}$)$_2$, —P(=O)(R$^{ee}$)$_2$, —OP (=O)(R$^{ee}$)$_2$, —OP(=O)(OR$^{ee}$)$_2$, C$_{1-10}$ alkyl, C$_{1-10}$ perhaloalkyl, C$_{1-10}$ alkenyl, C$_{1-10}$ alkynyl, heteroC$_{1-10}$alkyl, heteroC$_{1-10}$alkenyl, heteroC$_{1-10}$alkynyl, C$_{3-10}$ carbocyclyl, 3-10 membered heterocyclyl, C$_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents are joined to form =O or =S; wherein X$^-$ is a counterion;

each instance of R$^{ee}$ is, independently, selected from C$_{1-10}$ alkyl, C$_{1-10}$ perhaloalkyl, C$_{1-10}$ alkenyl, C$_{1-10}$ alkynyl, heteroC$_{1-10}$ alkyl, heteroC$_{1-10}$ alkenyl, heteroC$_{1-10}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_{6-10}$ aryl, and 5-10 membered heteroaryl, or two e groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; and each X$^-$ is a counterion.

In certain embodiments, each carbon atom substituent is independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, each carbon atom substituent is independently halogen, substituted (e.g., substituted with one or more halogen) or unsubstituted $C_{1-10}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts). In certain embodiments, each carbon atom substituent is independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, or —NO$_2$. In certain embodiments, each carbon atom substituent is independently halogen, substituted (e.g., substituted with one or more halogen moieties) or unsubstituted $C_{1-10}$ alkyl, —OR$^{aa}$, —SR$^{aa}$, —N(R$^{bb}$)$_2$, —CN, —SCN, or —NO$_2$, wherein R$^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each R$^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts).

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=S)OR$^{aa}$, —SC(=S) N(R$^{bb}$)$_2$, —SC(=O)SR$^{aa}$, —SC(=O)OR$^{aa}$, —SC(=O)N(R$^{bb}$)$_2$, and —SC(=O)R$^{aa}$, wherein R$^{aa}$ and R$^{cc}$ are as defined herein.

The term "amino" refers to the group —NH$_2$. The term "amino" is used interchangeably with the term "free amine." The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}$CO$_2R^{aa}$, —$NR^{bb}$C(=O)N($R^{bb}$)$_2$, —$NR^{bb}$C(=N$R^{bb}$)N($R^{bb}$)$_2$, —$NR^{bb}$SO$_2R^{aa}$, —$NR^{bb}$P(=O)(O$R^{cc}$)$_2$, and —$NR^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$X$^-$, wherein $R^{bb}$ and X$^-$ are as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers to a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-20}$ alkyl, $C_{1-20}$ perhaloalkyl, $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, each nitrogen atom substituent is independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or a nitrogen protecting group. In certain embodiments, each nitrogen atom substituent is independently substituted (e.g., substituted with one or more halogen) or unsubstituted $C_{1-10}$ alkyl, —C(=O)$R^{aa}$, —CO$_2R^{aa}$, —C(=O)N($R^{bb}$)$_2$, or a nitrogen protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each nitrogen atom substituent is independently substituted (e.g., substituted with one or more halogen) or unsubstituted $C_{1-6}$ alkyl or a nitrogen protecting group.

In certain embodiments, the substituent present on the nitrogen atom is a nitrogen protecting group (also referred to herein as an "amino protecting group"). Nitrogen protecting groups include —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$R", —SO$_2$O$R^{aa}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, in certain embodiments, at least one nitrogen protecting group is an amide group (e.g., a moiety that include the nitrogen atom to which the nitrogen protecting groups (e.g., —C(=O)$R^{aa}$) is directly attached). In certain such embodiments, each nitrogen protecting group, together with the nitrogen atom to which the nitrogen protecting group is attached, is independently selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivatives, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3- nitrobutanamide, o-nitrocinnamide, N-acetylmethionine derivatives, o-nitrobenzamide, and o-(benzoyloxymethyl)benzamide.

In certain embodiments, at least one nitrogen protecting group is a carbamate group (e.g., a moiety that include the nitrogen atom to which the nitrogen protecting groups (e.g., —C(=O)OR$^{aa}$) is directly attached). In certain such embodiments, each nitrogen protecting group, together with the nitrogen atom to which the nitrogen protecting group is attached, is independently selected from the group consisting of methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

In certain embodiments, at least one nitrogen protecting group is a sulfonamide group (e.g., a moiety that include the nitrogen atom to which the nitrogen protecting groups (e.g., —S(=O)$_2$R$^{aa}$) is directly attached). In certain such embodiments, each nitrogen protecting group, together with the nitrogen atom to which the nitrogen protecting group is attached, is independently selected from the group consisting of p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

In certain embodiments, each nitrogen protecting group, together with the nitrogen atom to which the nitrogen protecting group is attached, is independently selected from the group consisting of phenothiazinyl-(10)-acyl derivatives, N'-p-toluenesulfonylaminoacyl derivatives, N'-phenylaminothioacyl derivatives, N-benzoylphenylalanyl derivatives, N-acetylmethionine derivatives, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivatives, N-diphenylborinic acid derivatives, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In some embodiments, two instances of a nitrogen protecting group together with the nitrogen atoms to which the nitrogen protecting groups are attached are N,N'-isopropylidenediamine.

In certain embodiments, at least one nitrogen protecting group is Bn, Boc, Cbz, Fmoc, trifluoroacetyl, triphenylmethyl, acetyl, or Ts.

In certain embodiments, each oxygen atom substituent is independently substituted (e.g., substituted with one or more halogen) or unsubstituted C$_{1-10}$ alkyl, —C(=O)R$^{aa}$, —CO$_2$R$^{aa}$, —C(=O)N(R$^{bb}$)$_2$, or an oxygen protecting group. In certain embodiments, each oxygen atom substituents is independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or an oxygen protecting group, wherein R$^{aa}$ is hydrogen, substituted (e.g., substituted with one or more halogen) or unsubstituted C$_{1-10}$ alkyl, or an oxygen protecting group when attached to an oxygen atom; and each R$^{bb}$ is independently hydrogen, substituted (e.g., substituted with one or more halogen) or unsubstituted C$_{1-10}$ alkyl, or an oxygen protecting group. In certain embodiments, each oxygen atom substituent is independently substituted (e.g., substituted with one or more halogen) or unsubstituted C$_{1-6}$ alkyl or an oxygen protecting group.

In certain embodiments, the substituent present on an oxygen atom is an oxygen protecting group (also referred to herein as an "hydroxyl protecting group"). Oxygen protecting groups include —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, each oxygen protecting group, together with the oxygen atom to which the oxygen protecting group is attached, is selected from the group consisting of methoxy, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl (PMB), 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-Dimethoxy-3'"-[N-(imidazolylmethyl)]trityl Ether (IDTr-OR), 4,4'-Dimethoxy-3'"-[N-(imidazolylethyl)carbamoyl]trityl Ether (IETr-OR), 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate (MTMEC-OR), 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, at least one oxygen protecting group is silyl, TBDPS, TBDMS, TIPS, TES, TMS, MOM, THP, t-Bu, Bn, allyl, acetyl, pivaloyl, or benzoyl.

In certain embodiments, each sulfur atom substituent is independently substituted (e.g., substituted with one or more halogen) or unsubstituted C$_{1-10}$ alkyl, —C(=O)R$^{aa}$, —CO$_2$R$^{aa}$, —C(=O)N(R$^{bb}$)$_2$, or a sulfur protecting group. In certain embodiments, each sulfur atom substituent is independently substituted (e.g., substituted with one or more halogen) or unsubstituted C$_{1-10}$ alkyl, —C(=O)R$^{aa}$, —CO$_2$R$^{aa}$, —C(=O)N(R$^{bb}$)$_2$, or a sulfur protecting group, wherein R$^{aa}$ is hydrogen, substituted (e.g., substituted with one or more halogen) or unsubstituted C$_{1-10}$ alkyl, or an oxygen protecting group when attached to an oxygen atom; and each R$^{bb}$ is independently hydrogen, substituted (e.g., substituted with one or more halogen) or unsubstituted C$_{1-10}$ alkyl, or a nitrogen protecting group. In certain embodiments, each sulfur atom substituent is independently substituted (e.g., substituted with one or more halogen) or unsubstituted C$_{1-6}$ alkyl or a sulfur protecting group.

In certain embodiments, the substituent present on a sulfur atom is a sulfur protecting group (also referred to as a "thiol protecting group"). In some embodiments, each sulfur protecting group is selected from the group consisting of —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)

($OR^{cc}$)$_2$, and —P(=O)(N($R^{bb}$)$_2$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, oxygen, nitrogen, and/or sulfur atoms. In certain embodiments, a substituent comprises 0, 1, 2, or 3 hydrogen bond donors. In certain embodiments, a substituent comprises 0, 1, 2, or 3 hydrogen bond acceptors.

A "counterion" or "anionic counterion" is a negatively charged group associated with a positively charged group in order to maintain electronic neutrality. An anionic counterion may be monovalent (e.g., including one formal negative charge). An anionic counterion may also be multivalent (e.g., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

A "leaving group" (LG) is an art-understood term referring to an atomic or molecular fragment that departs with a pair of electrons in heterolytic bond cleavage, wherein the molecular fragment is an anion or neutral molecule. As used herein, a leaving group can be an atom or a group capable of being displaced by a nucleophile. See e.g., Smith, March Advanced Organic Chemistry 6th ed. (501-502). Exemplary leaving groups include, but are not limited to, halo (e.g., fluoro, chloro, bromo, iodo) and activated substituted hydroxyl groups (e.g., —OC(=O)S$R^{aa}$, —OC(=O)$R^{aa}$, —OCO$_2$$R^{aa}$, —OC(=O)N($R^{bb}$)$_2$, OC(=N$R^{bb}$)$R^{aa}$, OC(=N$R^{bb}$)O$R^{aa}$, —OC(=N$R^{bb}$)N($R^{bb}$)$_2$, OS(=O)$R^{aa}$, —OSO$_2$$R^{aa}$, —OP($R^{cc}$)$_2$, —OP($R^{cc}$)$_3$, —OP(=O)$_2$$R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein). Additional examples of suitable leaving groups include, but are not limited to, halogen alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some embodiments, the leaving group is a sulfonic acid ester, such as toluenesulfonate (tosylate, -OTs), methanesulfonate (mesylate, -OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, -OTf). In some embodiments, the leaving group is a brosylate, such as p-bromobenzenesulfonyloxy. In some embodiments, the leaving group is a nosylate, such as 2-nitrobenzenesulfonyloxy. In some embodiments, the leaving group is a sulfonate-containing group. In some embodiments, the leaving group is a tosylate group. In some embodiments, the leaving group is a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "cross-linked" refers to two or more polymers that are joined by covalent bonds. In certain embodiments, the cross-linked polymers are covalently attached.

The term "hydrophobic moiety" refers to a molecule or a portion of a molecule that is non-polar. A hydrophobic moiety is a molecule or portion of a molecule that is typically made up of hydrogen and carbon with minimal oxygen and nitrogen content. Hydrophobic moieties may be aliphatic hydrocarbon chains and/or rings that do not have a positive or negative charge. Hydrophobic moieties, also referred to as lipophilic moieties, have a tendency to interact with other hydrophobic and lipophilic moieties, rather than with water or other polar atoms or groups. Octanol-water partition ratio is a common way of expressing the lipophilicity of a compound, and it is defined as the ratio of the concentration of a solute in a water-saturated octanolic phase to its concentration in an octanol-saturated aqueous phase. See, e.g., S. Amézqueta, et al., *Liquid-Phase Extraction*, Handbooks in Separation Science, 2020, pp. 183-208.

The term "activating agent" as used herein refers to any agent suitable for activating a carboxylic acid towards subsequent coupling. The activating agent may transform the carboxylic acid into a reactive intermediate (e.g., acyl chloride, mixed anhydride, carbonic anhydride, activated ester, NHS-ester). In some embodiments, the reactive intermediate incorporates a leaving group that is readily displaced following nucleophilic attack at the carbonyl carbon. An activating agent may enhance the electrophilicity of the carbonyl carbon. An activating agent may catalyze a coupling reaction at the carboxylic acid. Examples of activating agents include, but are not limited to, carbodiimides and salts thereof (e.g., N,N'-dicyclohexylcarbodiimide, N,N'-diisopropylcarbodiimide, 1-ethyl-3-(3-dimethylaminopropyl)carbodiimide), 1H-benzotriazoles and salts thereof, thionyl chloride, phosphorous pentachloride, triphosgene, triazines, N-ethoxycarbonyl-2-ethoxy-1,2-dihydroquinoline, pentafluorophenol, and chloroformates. See, e.g., E. Valeur, et al., Amide bond formation: beyond the myth of coupling reagents, *Chem. Soc. Rev.*, 2009, 38, 606-631, J. Otera, et al. Esterification, Methods, Reactions, and Applications, 2$^{nd}$ ed. Wiley-VCH: Weinheim, 2010, and M. Kazemi, et al., Thioester synthesis: recent adventures in the esterification of thiols, *J. Sulfur Chem.*, 2015, 36, 613-623.

The disclosure is not intended to be limited in any manner by the above exemplary listing of substituents. Additional terms may be defined in other sections of this disclosure.

Other Definitions

The following definitions are more general terms used throughout the present application. As used herein, the term "salt" refers to any and all salts, and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "cosmetically acceptable salt" refers to a salt suitable for use in contact with human or animal skin without toxicity, incompatibility, instability, allergic response, irritation, and the like. Cosmetically acceptable salts also include dermatologically acceptable salts. Cosmetically acceptable salts are well known in the art. See, e.g., International Cosmetic Ingredient Dictionary and Handbook, 12$^{th}$ ed., T. E. Gottschalck and J. E. Bailey, Eds., Washington: Cosmetic, Toiletry and Fragrance Association (CTFA), 2012, incorporated herein by reference. Cosmetically acceptable salts of the compounds of this disclosure include those derived from suitable inorganic and organic acids and bases. Examples of cosmetically acceptable salts formed with organic or inorganic acids include, but are not limited to, acetate, aspartate, benzenesulfonate, benzoate, bicarbonate, bitartrate, bromide, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, ketoglutarate, lactate, lactobionate, malate, maleate, malonate, mandelate, mesylate, methylbromide, methylnitrate, methylsulfate, mucate, napsylate, nitrate, oleate, oxalate, pamoate, pantothenate, perchlorate, phosphate/diphosphate, polygalacturonate, salicylate, stearate, subacetate, succinate, sulfate, tannate, tartrate, teoclate, tosylate, triethiodide, and trifluoroacetate. Cosmetically acceptable salts derived from appropriate organic or inorganic bases include, but are not limited to, aluminum, ammonium, alkyl ammonium, benzathine, calcium, chloroprocaine, choline, cobalt, iron, lithium, magnesium, meglumine, potassium, procaine, sodium, zinc, and other alkali or alkaline earth metal salts. Further non-limiting examples of suitable organic bases for the formation of cosmetically acceptable salts may include amino acids such as arginine and lysine, mono-, di-, or trihydroxyalkylamines (e.g., mono-, di-, and triethanolamine, guanidine), N-methylglucosamine, N-methylpiperazine, morpholine, ethylenediamine, N-benzylphenethylamine, tris(hydroxymethyl) aminomethane, and the like.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "skin" refers to the external tissue layer in humans and animals. Typically, the skin forms a protective barrier against water, UV light, pathogens, physical injury, and chemical agents. Skin comprises the epidermis, dermis, subcutaneous tissue layer, and associated cells, glands, mucous membranes, and connective tissue. The epidermis is the outermost layer of the skin, comprising five sub-layers: stratum corneum, transparent layer, granular layer, visible layer, and an embryonic (base) layer. The dermis is the inner layer between the epidermis and the subcutaneous tissue layer. The dermis comprises the papillary dermis and the reticular dermis and may include connective tissue, blood vessels, oil and sweat glands, nerves, and hair follicles. The subcutaneous tissue layer (hypodermis) is the innermost layer of the skin, comprising fat and a loose meshwork of connective tissue (e.g., collagen and elastic fibers). In certain embodiments, the term "skin" refers to the stratum corneum. In another embodiment, the term "skin" refers to the dermis. Skin is described in detail in *Anatomy, Skin (Integument)*, H. Yousef, M. Alhajj, and S. Sharma, StatPearls, StatPearls Publishing, 2020.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, severity of side effects, disease, or disorder, the identity, pharmacokinetics, and pharmacodynamics of the particular compound, the condition being treated, the mode, route, and desired or required frequency of administration, the species, age and health or general condition of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. In certain embodiments, the desired dosage is delivered three times a day, two times a day, once a day, every other day, every third day, every week, every two weeks, every three weeks, or every four weeks. In certain embodiments, the desired dosage is delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human comprises about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for treating a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for preventing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2%, or 1% of a given value or range of values.

Unless otherwise required by context, singular terms shall include pluralities, and plural terms shall include the singular.

DETAILED DESCRIPTION OF CERTAIN EMBODIMENTS

Recently, there has been a focus on utilizing lipids, the major components of the stratum corneum (SC), to enhance skin retention and permeability for reducing deep wrinkles.[24,25] Lipids are favorable since most lipids from natural fatty acids are non-toxic, non-irritating and non-allergenic.[26-28] Moreover, the fatty acid is more cost-effective and safer than other methods for improving permeation and retention of topical treatments, such as skin penetrating peptides[29] or sulfoxide-based solvents such as DMSO, or DMF.[30,31] Enhanced skin permeation of lipidated biological molecules can provide the opportunity to enhance skin permeation and retention properties of hyaluronic acid. Therefore, combining HA with lipid has great potential to enhance skin penetration and retention.

However, the conjugation of hydrophobic lipid to HA poses a significant challenge because HA is extremely hydrophilic and poorly soluble in most organic solvents. To solve this problem, various methods have been used to increase solubility of hyaluronic acid in organic solvents for obtaining homogeneous mixtures of HA and hydrophobic materials. For instance, polyethylene glycol (PEG) has been adapted for increasing HA's solubility in DMSO.[32] However, the mass of PEG used is 5 times higher than the mass of HA, and the final concentration of HA in the reaction is extremely low (0.1 g HA in 5 mL DMSO). With the above method, the production cost, the volume of PEG and purification pose challenges that make scalable production of functionalized HA difficult. Encapsulating HA within lipid particles may constitute an appropriate vehicle to deliver HA to the skin and preserve HA properties during storage. However, physical encapsulation can be affected by any changes in the environment of a micelle during formulation, storage, or use, leading the micelles to collapse. Hence, covalent conjugation lipid to HA, particularly through hydrolysis-resistant bonds, can make the chemical structure more stable under physiological conditions and provides longer storage life. Bioconjugation reactions can achieve highly selective modification forming a new covalent bond under mild conditions.[33,34] For use in the cosmetic or pharmaceutical industry, effective bioconjugation using scalable and cost-effective chemistry is required to transition a molecule into products.

Provided herein are compounds (e.g., compounds of Formula (I)), and pharmaceutically and cosmetically acceptable salts thereof, and pharmaceutical compositions and cosmetic compositions and kits thereof. Also provided herein are methods of treating and/or preventing a disease, disorder, or condition in a subject comprising administering a therapeutically effective amount of a compound or composition provided herein to the subject. The compound or composition may be administered as a monotherapy or in combination with another therapy, as described herein. Also described herein are methods of preparing compounds of Formula (I) and synthetic intermediates useful to that end.

Compounds

Provided herein are compounds of Formula (I):

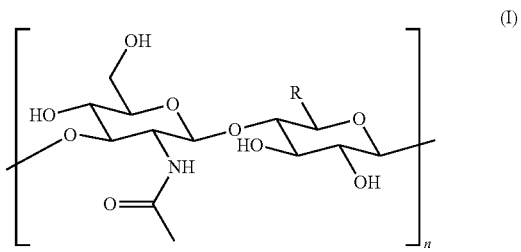

(I)

and pharmaceutically or cosmetically acceptable salts thereof, wherein:
n is an integer from 1-20,000;
each R is independently —CO$_2$H, or a group comprising a hydrophobic moiety; and
provided that at least 1% of R groups comprise a hydrophobic moiety.

As defined herein, each R is independently —CO$_2$H, or a group comprising a hydrophobic moiety.

In certain embodiments, when R a group comprising a hydrophobic moiety, R is of Formula (II):

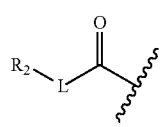

(II)

wherein
each L is independently substituted or unsubstituted aliphatic, or substituted or unsubstituted heteroaliphatic; and
each R$_2$ is independently substituted or unsubstituted aliphatic, substituted or unsubstituted heteroaliphatic, substituted or unsubstituted aryl, substituted or unsubstituted heteroaryl, or a combination thereof.

In certain embodiments, at least 1% of R groups are of Formula (II). In some embodiments, at least 2% of R groups are of formula (II). In certain embodiments, at least 5% of R groups are of Formula (II). In some embodiments, 1-20% of R groups are of Formula (II). In certain embodiments, 1-10% of R groups are of Formula (II). In some embodiments, 1-5% of R groups are of Formula (II). In certain embodiments, 5-10% of R groups are of Formula (II). In some embodiments, 10-20% of R groups are of Formula (II). In certain embodiments, 10-15% of R groups are of Formula (II). In some embodiments, 15-20% of R groups are of Formula (II).

As defined herein, Formula (I) represents a repeat unit, and the number of repeat units is indicated by the integer n. One skilled in the art will appreciate that at the termini of compounds of Formula (I), the broken bonds on the left and right are attached to suitable end groups. In certain embodiments, the broken bond on the left is attached to —H, -Me, or -Et. In some embodiments, the broken bond on the right is attached to —OH, —OMe, or —OEt. In certain embodiments, the broken bond on the left is attached to —H. In some embodiments, the broken bond on the right is attached to —OH. In certain embodiments, the broken bond on the left is attached to —H, and the broken bond on the right is attached to —OH. In some embodiments, compounds of Formula (I) are of Formula (Ic):

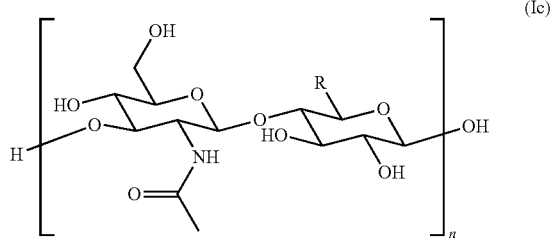

(Ic)

and pharmaceutically or cosmetically acceptable salts thereof, wherein:
n is an integer from 1-20,000;
each R is independently —CO$_2$H, or a group comprising a hydrophobic moiety; and
provided that at least 1% of R groups comprise a hydrophobic moiety.

As defined herein, n is an integer from 1-20,000. In some embodiments, n is an integer from 1-10,000. In certain embodiments, n is an integer from 1-5,000. In some embodiments, n is an integer from 1-20,000. In certain embodiments, n is an integer from 1-1,000. In some embodiments, n is an integer from 1-500. In certain embodiments, n is an integer from 1-300. In certain embodiments, n is an integer from 1-100. In some embodiments, n is an integer from 1-80. In certain embodiments n is an integer from 1-50. In some embodiments, n is an integer from 1-40. In certain embodiments, n is an integer from 1-30. In certain embodiments, n is an integer from 1-20. In some embodiments, n is an integer from 1-10. In certain embodiments, n is an integer from 10-50. In some embodiments, n is an integer from 10-20. In certain embodiments, n is an integer from 20-30. In some embodiments, n is an integer from 30-40. In certain embodiments, n is an integer from 40-50. In some embodiments, n is an integer from 5-20,000. In certain embodiments, n is an integer from 5-10,000. In some embodiments, n is an integer from 5-5,000. In certain embodiments, n is an integer from 5-2,000. In some embodiments, n is an integer from 5-1,000. In some embodiments, n is an integer from 5-300. In some embodiments, n is an integer from 5-100. In certain embodiments, n is an integer from 5-50. In some embodiments, n is an integer from 100-20,000. In certain embodiments, n is an integer from 100-10,000. In some embodiments, n is an integer from 100-1,000. In certain embodiments, n is an integer from 100-500.

As defined herein, each L is independently substituted or unsubstituted aliphatic, or substituted or unsubstituted heteroaliphatic. In certain embodiments, L is substituted aliphatic. In some embodiments, L is $C_{1-20}$ substituted aliphatic. In certain embodiments, L is $C_{1-12}$ substituted aliphatic. In some embodiments, L is $C_{1-6}$ substituted aliphatic. In certain embodiments, L is unsubstituted aliphatic. In some embodiments, L is $C_{1-20}$ unsubstituted aliphatic. In certain embodiments, L is $C_{1-12}$ unsubstituted aliphatic. In some embodiments, L is $C_{1-6}$ unsubstituted aliphatic. In certain embodiments, L is substituted heteroaliphatic. In some embodiments, L is unsubstituted $C_{2-20}$ heteroaliphatic. In certain embodiments, L is unsubstituted $C_{2-12}$ heteroaliphatic. In some embodiments, L is unsubstituted $C_{2-6}$ heteroaliphatic. In some embodiments, L is unsubstituted $C_{2-20}$ heteroaliphatic comprising one or more nitrogen, oxygen, or sulfur atoms. In certain embodiments, L is unsubstituted heteroaliphatic. In some embodiments, L is unsubstituted $C_{2-20}$ heteroaliphatic. In certain embodiments, L is unsubstituted heteroalkylene. In some embodiments, L is $C_{2-20}$ heteroalkylene. In certain embodiments, L is unsubstituted heteroalkylene comprising one or more nitrogen, oxygen, or sulfur atoms. In some embodiments, L is unsubstituted $C_{2-20}$ heteroalkylene comprising one or more nitrogen, oxygen, or sulfur atoms. In certain embodiments, L is unsubstituted $C_{2-12}$ heteroalkylene comprising one or more nitrogen, oxygen, or sulfur atoms. In some embodiments, L is unsubstituted $C_{2-6}$ heteroalkylene comprising one or more nitrogen, oxygen, or sulfur atoms. In certain embodiments, L is unsubstituted $C_2$ heteroalkylene comprising one or more nitrogen, oxygen, or sulfur atoms. In some embodiments, L is unsubstituted $C_3$ heteroalkylene comprising one or more nitrogen, oxygen, or sulfur atoms. In certain embodiments, L is unsubstituted $C_4$ heteroalkylene comprising one or more nitrogen, oxygen, or sulfur atoms. In some embodiments, L is unsubstituted $C_5$ heteroalkylene comprising one or more nitrogen, oxygen, or sulfur atoms. In certain embodiments, L is unsubstituted $C_6$ heteroalkylene comprising one or more nitrogen, oxygen, or sulfur atoms. In some embodiments, L is selected from the group consisting of:

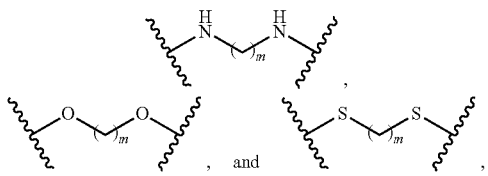

, and wherein m is 2-12. In certain embodiments, L is

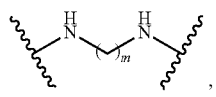

, wherein m is 2-12. In some embodiments, L is

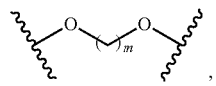

, wherein m is 2-12. In certain embodiments, L is

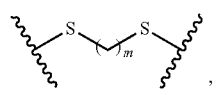

, wherein m is 2-12. In some embodiments, L is selected from the group consisting of 1,2-diaminoethyl, 1,3-diaminopropyl, 1,4-diaminobutyl, 1,5-diaminopentyl, and 1,6-diaminohexyl. In certain embodiments, L is selected from the group consisting of 1,2-diaminoethyl, 1,3-diaminopropyl, 1,4-diaminobutyl. In some embodiments, L is 1,2-diaminoethyl. In certain embodiments, L is 1,3-diaminopropyl. In some embodiments, L is 1,4-diaminobutyl.

As defined herein, each $R_2$ is independently substituted or unsubstituted aliphatic, substituted or unsubstituted heteroaliphatic, substituted or unsubstituted aryl, substituted or unsubstituted heteroaryl, or a combination thereof. In certain embodiments, $R_2$ comprises substituted or unsubstituted aliphatic. In certain embodiments, $R_2$ comprises unsubstituted aliphatic. In some embodiments, $R_2$ comprises unsubstituted $C_{1-40}$ aliphatic. In certain embodiments, $R_2$ comprises substituted alkyl. In some embodiments, $R_2$ comprises unsubstituted $C_{1-40}$ alkyl. In certain embodiments, $R_2$ comprises substituted alkenyl. In some embodiments, $R_2$ comprises unsubstituted $C_{1-40}$ alkenyl. In some embodiments, $R_2$ comprises substituted aliphatic. In some embodiments, $R_2$ comprises aliphatic substituted with a carbonyl. In certain embodiments, $R_2$ comprises substituted alkyl. In some embodiments, $R_2$ comprises substituted $C_{1-40}$ alkyl. In some embodiments, $R_2$ comprises $C_{1-40}$ alkyl substituted with a carbonyl. In certain embodiments, $R_2$ comprises substituted alkenyl. In some embodiments, $R_2$ comprises substituted $C_{1-40}$ alkenyl. In some embodiments, $R_2$ comprises $C_{1-40}$ alkenyl substituted with a carbonyl. In certain embodiments, $R_2$ comprises substituted or unsubstituted heteroaliphatic. In some embodiments, $R_2$ comprises substituted heteroaliphatic. In certain embodiments, $R_2$ comprises unsubstituted heteroaliphatic. In some embodiments, $R_2$ comprises unsubstituted $C_{1-10}$ heteroaliphatic. In some embodiments, $R_2$ comprises substituted $C_{1-40}$ heteroaliphatic. In certain embodiments, $R_2$ comprises substituted or unsubstituted aryl. In some embodiments, $R_2$ comprises substituted aryl. In certain embodiments, $R_2$ comprises substituted $C_{6-14}$ aryl. In some embodiments, $R_2$ comprises unsubstituted aryl. In certain embodiments, $R_2$ comprises unsubstituted $C_{6-14}$ aryl. In certain embodiments, $R_2$ comprises substituted or unsubstituted heteroaryl. In some embodiments, $R_2$ comprises substituted heteroaryl. In certain embodiments, $R_2$ comprises substituted $C_{5-8}$ heteroaryl. In some embodiments, $R_2$ comprises unsubstituted heteroaryl. In certain embodiments, $R_2$ comprises unsubstituted $C_{5-8}$ heteroaryl.

In some embodiments, $R_2$ is a fatty acid residue of the formula $—C(O)R_3$, wherein $R_3$ is substituted or unsubstituted aliphatic.

As defined herein, $R_3$ is substituted or unsubstituted aliphatic. In certain embodiments, $C_{8-35}$ aliphatic. In some embodiments, $R_3$ is $C_9$-$C_{19}$ aliphatic. In certain embodiments, $R_3$ is $C_{11}$ aliphatic. In some embodiments, $R_3$ is substituted or unsubstituted alkyl. In some embodiments, $R_3$ is substituted $C_{8-35}$ alkyl. In some embodiments, $R_3$ is substituted $C_9$-$C_{19}$ alkyl. In some embodiments, $R_3$ is unsubstituted $C_{8-35}$ alkyl. In certain embodiments, $R_3$ is unsubstituted $C_9$-$C_{19}$ alkyl. In certain embodiments, $R_3$ is unsubstituted $C_9$ alkyl. In some embodiments, $R_3$ is unsubstituted $C_{10}$ alkyl. In certain embodiments, $R_3$ is unsubstituted $C_{11}$ alkyl. In some embodiments, $R_3$ is unsubstituted $C_{12}$ alkyl. In certain embodiments, $R_3$ is unsubstituted $C_{13}$ alkyl. In some embodiments, $R_3$ is unsubstituted $C_{14}$ alkyl. In certain embodiments, $R_3$ is unsubstituted $C_{15}$ alkyl. In some embodiments, $R_3$ is unsubstituted $C_{16}$ alkyl. In certain embodiments, $R_3$ is unsubstituted $C_{1-7}$ alkyl. In some embodiments, $R_3$ is unsubstituted $C_{18}$ alkyl. In certain embodiments, $R_3$ is unsubstituted $C_{19}$ alkyl. In some embodiments, $R_3$ is substituted or unsubstituted alkenyl. In some embodiments, $R_3$ is substituted $C_{8-35}$ alkenyl. In some embodiments, $R_3$ is substituted $C_9$-$C_{19}$ alkenyl. In some embodiments, $R_3$ is unsubstituted $C_{8-35}$ alkenyl. In certain embodiments, $R_3$ is unsubstituted $C_9$-$C_{19}$ alkenyl. In certain embodiments, $R_3$ is unsubstituted $C_9$ alkenyl. In some embodiments, $R_3$ is unsubstituted $C_{10}$ alkenyl. In certain embodiments, $R_3$ is unsubstituted $C_{11}$ alkenyl. In some embodiments, $R_3$ is unsubstituted $C_{12}$ alkenyl. In certain embodiments, $R_3$ is unsubstituted $C_{13}$ alkenyl. In some embodiments, $R_3$ is unsubstituted $C_{14}$ alkenyl. In certain embodiments, $R_3$ is unsubstituted $C_{15}$ alkenyl. In some embodiments, $R_3$ is unsubstituted $C_{16}$ alkenyl. In certain embodiments, $R_3$ is unsubstituted $C_{17}$ alkenyl. In some embodiments, $R_3$ is unsubstituted $C_{18}$ alkenyl. In certain embodiments, $R_3$ is unsubstituted $C_{19}$ alkenyl.

In certain embodiments, the compound of Formula (I) is of the following formula:

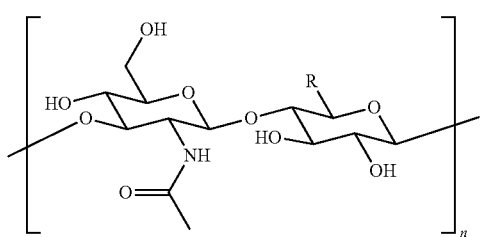
(I)

or a pharmaceutically or cosmetically acceptable salt thereof, wherein:
n is an integer from 5-50;
each R is independently —CO$_2$H, or a group of Formula (II):

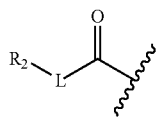
(II)

wherein L is

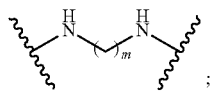
;

m is 2-12;
R$_2$ is a fatty acid residue of the formula —C(O)R$_3$, wherein R$_3$ is C$_{9-19}$ unsubstituted alkyl; and
provided that at least 1% of R groups comprise a group of Formula (II).

In certain embodiments, the compound of Formula (I) is of the following formula:

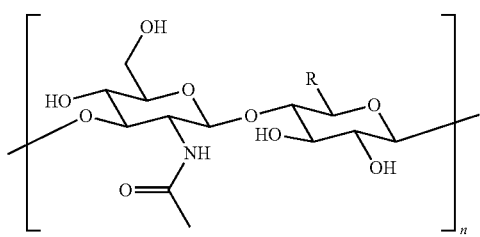
(I)

or a pharmaceutically or cosmetically acceptable salt thereof, wherein:
n is an integer from 5-50;
each R is independently —CO$_2$H, or a group of Formula (II):

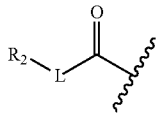
(II)

wherein L is

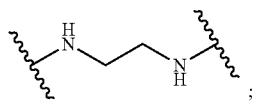 [SMILES: *NCCN*]
;

R$_2$ is a fatty acid residue of the formula —C(O)R$_3$, wherein R$_3$ is C$_{9-19}$ unsubstituted alkyl; and
provided that at least 1% of R groups comprise a group of Formula (II).

In certain embodiments, a compound of Formula (I) has the structure:

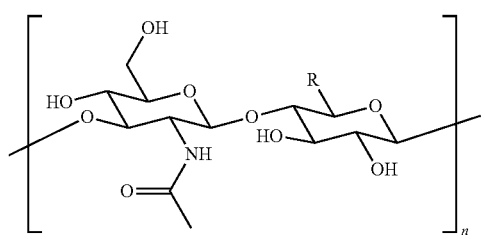
(I)

or a pharmaceutically or cosmetically acceptable salt thereof, wherein:
n is an integer from 5-50;
each R is independently —CO$_2$H, or a group of Formula (II):

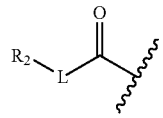
(II)

wherein L is

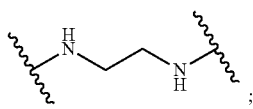 [SMILES: *NCCN*]
;

R$_2$ is a fatty acid residue of the formula —C(O)R$_3$, wherein R$_3$ is C$_{11}$ unsubstituted alkyl; and
provided that at least 1% of R groups comprise a group of formula (II).

In certain embodiments, a compound of Formula (I), or a pharmaceutically or cosmetically acceptable salt thereof, is characterized as having increased skin penetration and/or increased skin retention relative to unmodified hyaluronic acid of Formula (Ia):

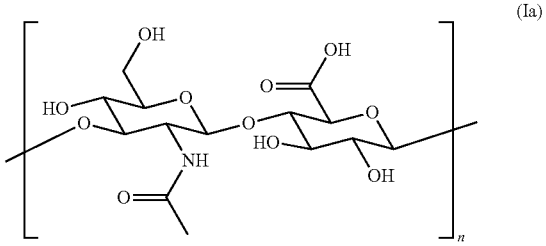

(Ia)

or a salt thereof, wherein n is an integer from 1-20,000. In some embodiments, a compound of Formula (I), or a pharmaceutically or cosmetically acceptable salt thereof, is characterized as having increased skin penetration and/or increased skin retention relative to unmodified hyaluronic acid of Formula (Ia), or a salt thereof, wherein n is an integer from 1-30. In certain embodiments, a compound of Formula (I), or a pharmaceutically or cosmetically acceptable salt thereof, is characterized as having increased skin penetration and/or increased skin retention relative to unmodified hyaluronic acid of Formula (Ia), or a salt thereof, by labeling the compounds with FITC, applying to a skin sample, and evaluating by confocal laser scanning microscopy (see "Skin Penetration and Retention Assays" in the Examples and FIG. 5).

In certain embodiments, the skin penetration and/or skin retention of a compound of Formula (I), or a pharmaceutically or cosmetically acceptable salt thereof, is increased for 1-90 hours. In some embodiments, the skin penetration and/or skin retention of a compound of Formula (I), or a pharmaceutically or cosmetically acceptable salt thereof, is increased for at least 1, 2, 4, 6, 8, 12, 16, 20, 24, 36, 48, 72, or 96 hours. In certain embodiments, the skin penetration and/or skin retention of a compound of Formula (I), or a pharmaceutically or cosmetically acceptable salt thereof, is increased for at least 1 hour. In some embodiments, the skin penetration and/or skin retention of a compound of Formula (I), or a pharmaceutically or cosmetically acceptable salt thereof, is increased for at least 2 hours. In certain embodiments, the skin penetration and/or skin retention of a compound of Formula (I), or a pharmaceutically or cosmetically acceptable salt thereof, is increased for at least 4 hours. In some embodiments, the skin penetration and/or skin retention of a compound of Formula (I), or a pharmaceutically or cosmetically acceptable salt thereof, is increased for at least 6 hours. In certain embodiments, the skin penetration and/or skin retention of a compound of Formula (I), or a pharmaceutically or cosmetically acceptable salt thereof, is increased for at least 8 hours. In some embodiments, the skin penetration and/or skin retention of a compound of Formula (I), or a pharmaceutically or cosmetically acceptable salt thereof, is increased for at least 12 hours. In certain embodiments, the skin penetration and/or skin retention of a compound of Formula (I), or a pharmaceutically or cosmetically acceptable salt thereof, is increased for at least 24 hours. In some embodiments, the skin penetration and/or skin retention of a compound of Formula (I), or a pharmaceutically or cosmetically acceptable salt thereof, is increased for at least 36 hours. In certain embodiments, the skin penetration and/or skin retention of a compound of Formula (I), or a pharmaceutically or cosmetically acceptable salt thereof, is increased for at least 48 hours. In some embodiments, the skin penetration and/or skin retention of a compound of Formula (I), or a pharmaceutically or cosmetically acceptable salt thereof, is increased for at least 72 hours. In certain embodiments, the skin penetration and/or skin retention of a compound of Formula (I), or a pharmaceutically or cosmetically acceptable salt thereof, is increased for at least 96 hours.

Pharmaceutical and Cosmetic Compositions, Kits, and Administration

The present disclosure provides compositions comprising a compound of Formula (I), or a pharmaceutically or cosmetically acceptable salt thereof, and optionally a pharmaceutically acceptable carrier or excipient. In certain embodiments, the composition described herein comprises a compound of Formula (I), or a pharmaceutically acceptable salt thereof, and a pharmaceutically acceptable carrier or excipient. In certain embodiments, the composition described is a pharmaceutical composition. In some embodiments, the composition described herein is a cosmetic composition.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. In certain embodiments, the effective amount is an amount effective for preventing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. In certain embodiments, the effective amount is an amount effective for reducing the risk of developing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, dehydration, pruritus (itch), or wrinkles) in a subject in need thereof.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit. In certain embodiments, a pharmaceutical composition described herein could be prepared according to the known method such as a method described in the general rules for preparations of the *Japanese Pharmacopoeia*, 16th edition, the *United States Pharmacopoeia, and the European Pharmacopoeia*, 9th edition. A pharmaceutical composition of the invention could be administered to patients appropriately depending on the dosage form.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate)(Veegum°, and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Dosage forms for topical and/or transdermal administration of a compound described herein may include ointments, balms, pastes, creams, lotions, gels, powders, solutions, emulsions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single topical dose) or multiple doses (e.g., multiple topical doses). In certain embodiments, when multiple doses are administered to a subject or applied to a tissue or cell, any two doses of the multiple doses include different or substantially the same amounts of a compound described herein.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional cosmetic agents. The compounds or compositions can be administered in combination with additional pharmaceutical agents that improve their activity (e.g., skin penetration, skin retention, and/or skin hydration). The compound or composition can be administered concurrently with, prior to, or subsequent to one or more additional cosmetic agents. Cosmetic agents include any ingredients that are appropriate for cosmetically treating, providing nutrients to, and/or conditioning the hair, nails, and/or skin. Cosmetic agents include, but are not limited to skin lightening agents, sunscreen agents, skin conditioning agents, skin protectants, emollients, humectants, colorants, pigments, fragrances, moisturizers, viscosity modifiers, anti-acne agents, vitamin B3 compound, peptide, antioxidant, radical scavenger, chelating agent, anti-inflammatory agent, local anesthetic, anti-cellulite agent, flavonoid, anti-bacterial agent, skin sedative, skin rejuvenating agent, anti-fungal agent, thickeners, antiperspirant agent, sensory agent, anti-dandruff agent, or mixtures thereof. See, e.g., International Cosmetic Ingredient Dictionary and Handbook, $12^{th}$ ed., T. E. Gottschalck and J. E. Bailey, Eds., Washington: Cosmetic, Toiletry and Fragrance Association (CTFA), 2012.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, in improving bioavailability, improving safety, reducing drug resistance, reducing and/or modifying metabolism, inhibiting excretion, and/or modifying distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both. In some embodiments, the additional pharmaceutical agent achieves a desired effect for the same disorder. In some embodiments, the additional pharmaceutical agent achieves different effects.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles). Each additional pharmaceutical agent may be administered at a dose and/or on a time schedule determined for that pharmaceutical agent. The additional pharmaceutical agents may also be administered together with each other and/or with the compound or composition described herein in a single dose or composition or administered separately in different doses or compositions. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, steroidal or non-steroidal anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, anesthetics, anti-coagulants, inhibitors of an enzyme, steroidal agents, steroidal or antihistamine, antigens, vaccines, antibodies, decongestant, sedatives, opioids, analgesics, anti-pyretics, hormones, and prostaglandins.

Additional pharmaceutical agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the pharmaceutical composition or cosmetic composition is a solution, emulsion, cream, lotion, ointment, balm, gel, paste, powder, spray, inhalant, or patch. In some embodiments, the pharmaceutical composition or cosmetic composition is a solution. In certain embodiments, the pharmaceutical composition or cosmetic composition is an emulsion. In some embodiments, the pharmaceutical composition or cosmetic composition is a cream. In certain embodiments, the pharmaceutical composition or cosmetic composition is a lotion. In some embodiments, the pharmaceutical composition or cosmetic composition is an ointment. In certain embodiments, the pharmaceutical composition or cosmetic composition is a balm. In some embodiments, the pharmaceutical composition or cosmetic composition is a gel. In certain embodiments, the pharmaceutical composition or cosmetic composition is a paste. In some embodiments, the pharmaceutical composition or cosmetic composition is a powder. In certain embodiments, the pharmaceutical composition or cosmetic composition is a spray. In some embodiments, the pharmaceutical composition or cosmetic composition is an inhalant. In certain embodiments, the pharmaceutical composition or cosmetic composition is a patch.

In certain embodiments, the composition comprises 0.001-99 wt % of the compound of Formula (I) or pharmaceutically or cosmetically acceptable salt thereof. In some embodiments, the composition comprises 0.001-75 wt % of the compound of Formula (I) or pharmaceutically or cosmetically acceptable salt thereof. In certain embodiments, the composition comprises 0.001-50 wt % of the compound of Formula (I) or pharmaceutically or cosmetically acceptable salt thereof. In some embodiments, the composition comprises 0.001-25 wt % of the compound of Formula (I) or pharmaceutically or cosmetically acceptable salt thereof. In certain embodiments, the composition comprises 0.001-10 wt % of the compound of Formula (I) or pharmaceutically or cosmetically acceptable salt thereof. In some embodiments, the composition comprises 0.001-2 wt % of the compound of Formula (I) or pharmaceutically or cosmetically acceptable salt thereof. In certain embodiments, the composition comprises 0.001-1 wt % of the compound of Formula (I) or pharmaceutically or cosmetically acceptable salt thereof. In some embodiments, the composition comprises 0.001-0.5 wt % of the compound of Formula (I) or pharmaceutically or cosmetically acceptable salt thereof. In certain embodiments, the composition comprises 0.1-2 wt % of the compound of Formula (I) or pharmaceutically or cosmetically acceptable salt thereof. In some embodiments, the composition comprises 0.001-0.2 wt % of the compound of Formula (I) or pharmaceutically or cosmetically acceptable salt thereof. In certain embodiments, the composition comprises 0.2-0.4 wt % of the compound of Formula (I) or pharmaceutically or cosmetically acceptable salt thereof. In some embodiments, the composition comprises 0.4-0.6 wt % of the compound of Formula (I) or pharmaceutically or cosmetically acceptable salt thereof. In certain embodiments, the composition comprises 0.6-0.8 wt % of the compound of Formula (I) or pharmaceutically or cosmetically acceptable salt thereof. In some embodiments, the composition comprises 0.8-1 wt % of the compound of Formula (I) or pharmaceutically or cosmetically acceptable salt thereof. In certain embodiments, the composition comprises 1-1.2 wt % of the compound of Formula (I) or pharmaceutically or cosmetically acceptable salt thereof. In some embodiments, the composition comprises 1.2-1.4 wt % of the compound of Formula (I) or pharmaceutically or cosmetically acceptable salt thereof. In certain embodiments, the composition comprises 1.4-1.6 wt % of the compound of Formula (I) or pharmaceutically or cosmetically acceptable salt thereof. In some embodiments, the composition comprises 1.6-1.8 wt % of the compound of Formula (I) or pharmaceutically or cosmetically acceptable salt thereof. In certain embodiments, the composition comprises 1.8-2 wt % of the compound of Formula (I) or pharmaceutically or cosmetically acceptable salt thereof.

In some embodiments, the composition comprising a compound of Formula (I), or a pharmaceutically or cosmetically acceptable salt thereof, is characterized as having increased skin penetration relative to unmodified hyaluronic acid of Formula (Ia), or a salt thereof. In certain embodiments, the composition comprising a compound of Formula (I), or a pharmaceutically or cosmetically acceptable salt thereof, is characterized as having increased skin penetration relative to unmodified hyaluronic acid of Formula (Ia), or a salt thereof, by labeling the compounds with FITC, applying to a skin sample, and evaluating by confocal laser scanning microscopy (see "Skin Penetration and Retention Assays" in the Examples and FIG. 5).

In certain embodiments, the skin penetration is increased by 1-300%. In some embodiments, the skin penetration is increased by 1-5%, 5-10%, 10-15%, 15-20%, 20-25%, 25-30%, 30-35%, 35-40%, 40-45%, 45-50%, 50-75%, 75-100%, 100-150%, 150-200%, 200-250%, or 250-300%. In certain embodiments, the skin penetration is increased by 1-5%. In some embodiments, the skin penetration is increased by 5-10%. In certain embodiments, the skin penetration is increased by 10-15%. In certain embodiments, the skin penetration is increased by 15-20%. In some embodiments, the skin penetration is increased by 20-25%. In certain embodiments, the skin penetration is increased by 25-30%. In some embodiments, the skin penetration is increased by 30-35%. In certain embodiments, the skin penetration is increased by 35-40%. In some embodiments, the skin penetration is increased by 40-45%. In certain embodiments, the skin penetration is increased by 45-50%. In some embodiments, the skin penetration is increased by 50-75%. In certain embodiments, the skin penetration is increased by 75-100%. In some embodiments, the skin penetration is increased by 100-125%. In certain embodiments, the skin penetration is increased by 125-150%. In some embodiments, the skin penetration is increased by 150-200%. In certain embodiments, the skin penetration is increased by 200-250%. In some embodiments, the skin penetration is increased by 250-300%. In certain embodiments, the skin penetration is increased by at least 5%, 10%, 25%, 50%, or 100%. In some embodiments, the skin penetration is increased by at least 5%. In certain embodiments, the skin penetration is increased by at least 10%. In some embodiments, the skin penetration is increased by at least 25%. In certain embodiments, the skin penetration is increased by at least 50%. In some embodiments, the skin penetration is increased by at least 75%. In certain embodiments, the skin penetration is increased by at least 100%.

In certain embodiments, the increased skin penetration is characterized by permeation into the stratum corneum, stratum lucidum, stratum granulosum, stratum spinosum, stratum basale, or dermis. In some embodiments, the increased skin penetration is characterized by permeation into the stratum corneum or dermis. In certain embodiments, the increased skin penetration is characterized by permeation into the stratum corneum. In some embodiments, the increased skin penetration is characterized by permeation into the dermis.

In certain embodiments, the composition comprising a compound of Formula (I), or a pharmaceutically or cosmetically acceptable salt thereof, is characterized as having increased skin retention relative to unmodified hyaluronic acid of Formula (Ia), or a salt thereof. In certain embodiments, the composition comprising a compound of Formula (I), or a pharmaceutically or cosmetically acceptable salt thereof, is characterized as having increased skin retention relative to unmodified hyaluronic acid of Formula (Ia), or a salt thereof, by labeling the compounds with FITC, applying to a skin sample, and evaluating by confocal laser scanning microscopy (see "Skin Penetration and Retention Assays" in the Examples and FIG. 5).

In certain embodiments, the skin retention is increased by 1-300%. In some embodiments, the skin retention is increased by 1-5%, 5-10%, 10-15%, 15-20%, 20-25%, 25-30%, 30-35%, 35-40%, 40-45%, 45-50%, 50-75%, 75-100%, 100-150%, 150-200%, 200-250%, or 250-300%. In certain embodiments, the skin retention is increased by 1-5%. In some embodiments, the skin retention is increased by 5-10%. In some embodiments, the skin retention is increased by 10-15%. In certain embodiments, the skin retention is increased by 15-20%. In some embodiments, the skin retention is increased by 20-25%. In certain embodiments, the skin retention is increased by 25-30%. In some embodiments, the skin retention is increased by 30-35%. In certain embodiments, the skin retention is increased by 35-40%. In some embodiments, the skin retention is increased by 40-45%. In certain embodiments, the skin retention is increased by 45-50%. In some embodiments, the skin retention is increased by 50-75%. In certain embodiments, the skin retention is increased by 75-100%. In some embodiments, the skin retention is increased by 100-125%. In certain embodiments, the skin retention is increased by 125-150%. In some embodiments, the skin retention is increased by 150-200%. In certain embodiments, the skin retention is increased by 200-250%. In some embodiments, the skin retention is increased by 250-300%. In certain embodiments, the skin retention is increased by at least 5%, 10%, 25%, 50%, or 100%. In some embodiments, the skin retention is increased by at least 5%. In certain embodiments, the skin retention is increased by at least 10%. In some embodiments, the skin retention is increased by at least 25%. In certain embodiments, the skin retention is increased by at least 50%. In some embodiments, the skin retention is increased by at least 100%.

In certain embodiments, the skin penetration is increased for 1-90 hours. In some embodiments, the skin penetration is increased for at least 1, 2, 4, 6, 8, 12, 16, 20, 24, 36, 48, 72, or 96 hours. In certain embodiments, the skin penetration is increased for at least 1 hour. In some embodiments, the skin penetration is increased for at least 2 hours. In certain embodiments, the skin penetration is increased for at least 4 hours. In some embodiments, the skin penetration is increased for at least 6 hours. In certain embodiments, the skin penetration is increased for at least 8 hours. In some embodiments, the skin penetration is increased for at least 12 hours. In certain embodiments, the skin penetration is increased for at least 24 hours. In some embodiments, the skin penetration is increased for at least 36 hours. In certain embodiments, the skin penetration is increased for at least 48 hours. In some embodiments, the skin penetration is increased for at least 72 hours. In certain embodiments, the skin penetration is increased for at least 96 hours.

In certain embodiments, the skin retention is increased for 1-90 hours. In some embodiments, the skin retention is increased for at least 1, 2, 4, 6, 8, 12, 16, 20, 24, 36, 48, 72, or 96 hours. In certain embodiments, the skin retention is increased for at least 1 hour. In some embodiments, the skin retention is increased for at least 2 hours. In certain embodiments, the skin retention is increased for at least 4 hours. In some embodiments, the skin retention is increased for at least 6 hours. In certain embodiments, the skin retention is increased for at least 8 hours. In some embodiments, the skin retention is increased for at least 12 hours. In certain embodiments, the skin retention is increased for at least 24 hours. In some embodiments, the skin retention is increased for at least 36 hours. In certain embodiments, the skin retention is increased for at least 48 hours. In some embodiments, the skin retention is increased for at least 72 hours. In certain embodiments, the skin retention is increased for at least 96 hours.

In certain embodiments, the composition comprising a compound of Formula (I), or a pharmaceutically or cosmetically acceptable salt thereof, is characterized as being substantially free of free amines. In some embodiments, free amines are unreacted diaminoalkyl compounds or unreacted amine-functionalized HA. In certain embodiments, free amines are unreacted diaminoalkyl compounds. In some embodiments, free amines are unreacted amine-functionalized HA. In certain embodiments, free amines comprise less than 10% of N-containing moieties present in the composition. In some embodiments, free amines comprise less than 5% of N-containing moieties present in the composition. In certain embodiments, free amines comprise less than 2% of N-containing moieties present in the composition. In some embodiments, free amines comprise less than 1% of N-containing moieties present in the composition. In certain embodiments, free amines comprise less than 0.5% of N-containing moieties present in the composition. In some embodiments, free amines comprise less than 0.1% of N-containing moieties present in the composition.

In certain embodiments, the composition comprising a compound of Formula (I), or a pharmaceutically or cosmetically acceptable salt thereof, is characterized as being substantially free of cross-linked hyaluronic acid. In some embodiments, the composition comprising a compound of Formula (I), or a pharmaceutically or cosmetically acceptable salt thereof, is characterized as comprising fewer than three cross-links per chain. In certain embodiments, the composition comprising a compound of Formula (I), or a pharmaceutically or cosmetically acceptable salt thereof, is characterized as comprising fewer than two cross-links per chain.

In certain embodiments, the composition comprising a compound of Formula (I), or a pharmaceutically or cosmetically acceptable salt thereof, is characterized as non-cytotoxic. In some embodiments, the composition comprising a compound of Formula (I), or a pharmaceutically or cosmetically acceptable salt thereof, is characterized as non-cytotoxic by a cytotoxic assay. In certain embodiments, the composition comprising a compound of Formula (I), or a pharmaceutically or cosmetically acceptable salt thereof, is characterized as non-cytotoxic by a cytotoxic assay is performed in vitro. In some embodiments, the composition comprising a compound of Formula (I), or a pharmaceutically or cosmetically acceptable salt thereof, is characterized as non-cytotoxic by a cytotoxic assay comprising treating NIH 3T3 fibroblast cells with varying concentrations of hyaluronic acid or a compound of Formula (I), or a pharmaceutically or cosmetically acceptable salt thereof, incubating with a solution of 3-(4,5-dimethylthiazol-2-yl)-2,5-diphenyltetrazolium bromide (MTT), measuring the absorbance at 570 nm by a plate reader, and comparing to the absorbance observed for control cells (see "Cell Cytotoxicity and Immunogenicity Assays" in the Examples and FIG. 4B). In certain embodiments, the composition comprising a compound of Formula (I), or a pharmaceutically or cosmetically acceptable salt thereof, is characterized as non-cytotoxic by a cytotoxic assay, wherein the concentration of hyaluronic acid or a compound of Formula (I), or a pharmaceutically or cosmetically acceptable salt thereof, used in the cytotoxic assay comprises a maximum of 1 wt %. In some embodiments, the composition comprising a compound of Formula (I), or a pharmaceutically or cosmetically acceptable salt thereof, is characterized as non-cytotoxic by a cytotoxic assay, wherein the concentration of hyaluronic acid or a compound of Formula (I), or a pharmaceutically or cosmetically acceptable salt thereof, used in the cytotoxic assay comprises 0.1 wt %, 0.01 wt %, 0.001 wt %, 0.0001 wt %, or 0.00001 wt % (see FIG. 4B). In certain embodiments, the composition comprising a compound of Formula (I), or a pharmaceutically or cosmetically acceptable salt thereof, is characterized as non-cytotoxic, wherein cells treated with the composition exhibit at least 80% relative metabolic activity (see FIG. 4B). In certain embodiments, the composition comprising a compound of Formula (I), or a pharmaceutically or cosmetically acceptable salt thereof, is characterized as non-cytotoxic, wherein NIH 3T3 fibroblast cells treated with the composition exhibit at least 80% relative metabolic activity (see FIG. 4B).

In certain embodiments, the composition comprising a compound of Formula (I), or a pharmaceutically or cosmetically acceptable salt thereof, is characterized as non-immunogenic. In some embodiments, the composition comprising a compound of Formula (I), or a pharmaceutically or cosmetically acceptable salt thereof, is characterized as non-immunogenic by an immunogenicity assay. In certain embodiments, the composition comprising a compound of Formula (I), or a pharmaceutically or cosmetically acceptable salt thereof, is characterized by non-immunogenic by an immunogenicity assay performed in vitro. In some embodiments, the composition comprising a compound of Formula (I), or a pharmaceutically or cosmetically acceptable salt thereof, is characterized by non-immunogenic by an immunogenicity assay comprising treating NIH 3T3 fibroblast cells treated with varying concentrations of hyaluronic acid or a compound of Formula (I), or a pharmaceutically or cosmetically acceptable salt thereof, incubating at 37° C. with 5% $CO_2$, and measuring IL-6 production (see "Cell Cytotoxicity and Immunogenicity Assays" in the Examples and FIG. 4A). In certain embodiments, the composition comprising a compound of Formula (I), or a pharmaceutically or cosmetically acceptable salt thereof, is characterized by non-immunogenic by an immunogenicity assay wherein the concentration of hyaluronic acid or a compound of Formula (I), or a pharmaceutically or cosmetically acceptable salt thereof, used in the immunogenicity assay comprises a maximum of 1 wt %. In some embodiments, the composition comprising a compound of Formula (I), or a pharmaceutically or cosmetically acceptable salt thereof, is characterized by non-immunogenic by an immunogenicity assay wherein the concentration of hyaluronic acid or a compound of Formula (I), or a pharmaceutically or cosmetically acceptable salt thereof, used in the immunogenicity assay comprises 0.1 wt %, 0.01 wt %, 0.001 wt %, 0.0001 wt %, or 0.00001 wt % (see FIG. 4A). In certain embodiments, the composition comprising a compound of Formula (I), or a pharmaceutically or cosmetically acceptable salt thereof, is characterized as non-immunogenic, wherein cells treated with the composition produce less than 20 pg/mL IL-6 (see FIG. 4A). In some embodiments, the composition comprising a compound of Formula (I), or a pharmaceutically or cosmetically acceptable salt thereof, is characterized as non-immunogenic, wherein cells treated with the composition produce less than 15 pg/mL IL-6 (see FIG. 4A). In certain embodiments, the composition comprising a compound of Formula (I), or a pharmaceutically or cosmetically acceptable salt thereof, is characterized as non-immunogenic, wherein NIH 3T3 fibroblast cells treated with the composition produce less than 20 pg/mL IL-6 (see FIG. 4A). In some embodiments, the composition comprising a compound of Formula (I), or a pharmaceutically or cosmetically acceptable salt thereof, is characterized as non-immunogenic, wherein NIH 3T3 fibroblast cells treated with the composition produce less than 15 pg/mL IL-6 (see FIG. 4A).

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. In certain embodiments, the kits are useful for preventing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. In certain embodiments, the kits are useful for reducing the risk of developing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. In certain embodiments, the kits and instructions provide for preventing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. In certain embodiments, the kits and instructions provide for reducing the risk of developing a disease, disorder, or condition (e.g., skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles) in a subject in need thereof. A kit described herein may include one or more additional pharmaceutical agents described herein as a separate composition.

Methods of Treatment and Uses

Provided herein are methods of using the compounds provided herein (e.g., compounds of Formula (I)), and pharmaceutically or cosmetically acceptable salts thereof, and pharmaceutical compositions and cosmetic compositions thereof.

Provided herein are methods of treating and/or preventing a disease, disorder, or condition in a subject in need thereof, the methods comprising administering to the subject a compound of Formula (I), or a pharmaceutically or cosmetically acceptable salt thereof, or a pharmaceutical composition or cosmetic compositions thereof. In certain embodiments, the disease, disorder, or condition is skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles.

Also provided herein are uses of the compounds of Formula (I), and pharmaceutically and cosmetically acceptable salts thereof, and pharmaceutical and cosmetic compositions thereof, for the preparation of a medicament for treating and/or preventing a disease, disorder or condition in a subject. In certain embodiments, the disease, disorder, or condition is skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles.

Also provided herein are compounds of Formula (I), and pharmaceutically and cosmetically acceptable salts thereof, and pharmaceutical and cosmetic compositions thereof, for use in treating and/or preventing a disease in a subject. In certain embodiments, the disease, disorder, or condition is skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles.

In certain embodiments, the disease, disorder, or condition is skin cancer, lupus, seborrheic dermatitis, tinea, psoriasis, acne, rosacea, hyperseborrhea, xerosis, atopic dermatitis (eczema), sebaceous hyperplasia, sunburn, an open wound, burns, bed sores, skin ulcers, pruritus (itch), dehydration, or wrinkles. In some embodiments, the disease, disorder, or condition is skin cancer. In certain embodiments, the disease, disorder, or condition is lupus. In some embodiments, the disease, disorder, or condition is seborrheic dermatitis. In certain embodiments, the disease, disorder, or condition is tinea. In some embodiments, the disease, disorder, or condition is psoriasis. In some embodiments, the disease, disorder, or condition is acne. In certain embodiments, the disease, disorder, or condition is rosacea. In some embodiments, the disease, disorder, or condition is hyperseborrhea. In certain embodiments, the disease, disorder, or condition is xerosis. In some embodiments, the disease, disorder, or condition is atopic dermatitis (eczema). In certain embodiments, the disease, disorder, or condition is sebaceous hyperplasia. In some embodiments, the disease, disorder, or condition is sunburn. In certain embodiments, the disease, disorder, or condition is an open wound. In some embodiments, the disease, disorder, or condition is burns. In certain embodiments, the disease, disorder, or condition is bed sores. In some embodiments, the disease, disorder, or condition is skin ulcers. In certain embodiments, the disease, disorder, or condition is pruritus (itch). In some embodiments, the disease, disorder, or condition is dehydration. In some embodiments, the disease, disorder, or condition is wrinkles.

In certain embodiments, the disease, disorder, or condition is skin cancer. In some embodiments, the skin cancer is squamous cell carcinoma (SCC), keratoacanthoma (KA), melanoma, basal cell carcinoma (BCC), cutaneous T-cell lymphoma, dermatofibrosarcoma protuberans, Merkel cell carcinoma, sebaceous carcinoma, Kaposi sarcoma, actinic keratosis, or Bowen's disease. In certain embodiments, the skin cancer is squamous cell carcinoma (SCC), melanoma, or basal cell carcinoma (BCC). In some embodiments, the skin cancer is squamous cell carcinoma (SCC). In certain embodiments, the skin cancer is keratoacanthoma (KA). In some embodiments, the skin cancer is melanoma. In certain embodiments, the skin cancer is basal cell carcinoma (BCC). In some embodiments, the skin cancer is cutaneous T-cell lymphoma. In certain embodiments, the skin cancer is dermatofibrosarcoma protuberans. In some embodiments, the skin cancer is Merkel cell carcinoma. In certain embodiments, the skin cancer is sebaceous carcinoma. In some embodiments, the skin cancer is Kaposi sarcoma. In certain embodiments, the skin cancer is actinic keratosis. In some embodiments, the skin cancer is Bowen's disease. See, e.g., Z. Apalla, et al., Skin Cancer: Epidemiology, Disease Burden, Pathophysiology, Diagnosis, and Therapeutic Approaches, *Dermatol. Ther.* 2017, 7, 5-19 and K. V. Laikova, et al., Advances in the Understanding of Skin Cancer: Ultraviolet Radiation, Mutations, and Antisense Oligonucleotides as Anticancer Drugs.

In certain embodiments, the effective amount of the compound or pharmaceutically or cosmetically acceptable salts thereof, and pharmaceutical compositions and cosmetic compositions thereof is administered orally, parenterally, intramuscularly, subcutaneously, intravenously, topically, or transdermally. In some embodiments, the effective amount of the compound of Formula (I), or a pharmaceutically or cosmetically acceptable salt thereof, or a pharmaceutical composition or cosmetic composition thereof is administered orally. In certain embodiments, the effective amount of the compound of Formula (I), or a pharmaceutically or cosmetically acceptable salt thereof, or a pharmaceutical composition or cosmetic composition thereof is administered parenterally. In some embodiments, the effective amount of the compound of Formula (I), or a pharmaceutically or cosmetically acceptable salt thereof, or a pharmaceutical composition or cosmetic composition thereof is administered intramuscularly. In certain embodiments, the effective amount of the compound of Formula (I), or a pharmaceutically or cosmetically acceptable salt thereof, or a pharmaceutical composition or cosmetic composition thereof is administered subcutaneously. In some embodiments, the effective amount of the compound of Formula (I), or a pharmaceutically or cosmetically acceptable salt thereof, or a pharmaceutical composition or cosmetic composition thereof is administered intravenously. In certain embodiments, the effective amount of the compound of Formula (I), or a pharmaceutically or cosmetically acceptable salt thereof, or a pharmaceutical composition or cosmetic composition thereof is administered topically. In some embodiments, the effective amount of the compound of Formula (I) or pharmaceutically or cosmetically acceptable salts thereof, and pharmaceutical compositions and cosmetic compositions thereof is administered transdermally.

In certain embodiments, the pharmaceutical composition or cosmetic composition is a solution, emulsion, cream, lotion, ointment, balm, gel, paste, powder, spray, inhalant, or patch. In some embodiments, the pharmaceutical composition or cosmetic composition is a solution. In certain embodiments, the pharmaceutical composition or cosmetic composition is an emulsion. In some embodiments, the pharmaceutical composition or cosmetic composition is a cream. In certain embodiments, the pharmaceutical composition or cosmetic composition is a lotion. In some embodiments, the pharmaceutical composition or cosmetic composition is an ointment. In certain embodiments, the pharmaceutical composition or cosmetic composition is a balm. In some embodiments, the pharmaceutical composition or cosmetic composition is a gel. In certain embodiments, the pharmaceutical composition or cosmetic composition is a paste. In some embodiments, the pharmaceutical composition or cosmetic composition is a powder. In certain embodiments, the pharmaceutical composition or cosmetic composition is a spray. In some embodiments, the pharmaceutical composition or cosmetic composition is an inhalant. In certain embodiments, the pharmaceutical composition or cosmetic composition is a patch.

In certain embodiments, the pharmaceutical composition or cosmetic composition comprises 0.001-99 wt % of the compound of Formula (I) or pharmaceutically or cosmetically acceptable salt thereof. In some embodiments, the pharmaceutical composition or cosmetic composition comprises 0.001-75 wt % of the compound of Formula (I) or pharmaceutically or cosmetically acceptable salt thereof. In certain embodiments, the pharmaceutical composition or cosmetic composition comprises 0.001-50 wt % of the compound of Formula (I) or pharmaceutically or cosmetically acceptable salt thereof. In some embodiments, the pharmaceutical composition or cosmetic composition comprises 0.001-25 wt % of the compound of Formula (I) or pharmaceutically or cosmetically acceptable salt thereof. In certain embodiments, the pharmaceutical composition or cosmetic composition comprises 0.001-10 wt % of the compound of Formula (I) or pharmaceutically or cosmetically acceptable salt thereof. In some embodiments, the pharmaceutical composition or cosmetic composition comprises 0.001-2 wt % of the compound of Formula (I) or pharmaceutically or cosmetically acceptable salt thereof. In certain embodiments, the pharmaceutical composition or cosmetic composition comprises 0.001-1 wt % of the compound of Formula (I) or pharmaceutically or cosmetically acceptable salt thereof. In some embodiments, the pharmaceutical composition or cosmetic composition comprises 0.001-0.5 wt % of the compound of Formula (I) or pharmaceutically or cosmetically acceptable salt thereof. In certain embodiments, the pharmaceutical composition or cosmetic composition comprises 0.1-2 wt % of the compound of Formula (I) or pharmaceutically or cosmetically acceptable salt thereof. In some embodiments, the pharmaceutical composition or cosmetic composition comprises 0.001-0.2 wt % of the compound of Formula (I) or pharmaceutically or cosmetically acceptable salt thereof. In certain embodiments, the pharmaceutical composition or cosmetic composition comprises 0.2-0.4 wt % of the compound of Formula (I) or pharmaceutically or cosmetically acceptable salt thereof. In some embodiments, the pharmaceutical composition or cosmetic composition comprises 0.4-0.6 wt % of the compound of Formula (I) or pharmaceutically or cosmetically acceptable salt thereof. In certain embodiments, the pharmaceutical composition or cosmetic composition comprises 0.6-0.8 wt % of the compound of Formula (I) or pharmaceutically or cosmetically acceptable salt thereof. In some embodiments, the pharmaceutical composition or cosmetic composition comprises 0.8-1 wt % of the compound of Formula (I) or pharmaceutically or cosmetically acceptable salt thereof. In certain embodiments, the pharmaceutical composition or cosmetic composition comprises 1-1.2 wt % of the compound of Formula (I) or pharmaceutically or cosmetically acceptable salt thereof. In some embodiments, the pharmaceutical composition or cosmetic composition comprises 1.2-1.4 wt % of the compound of Formula (I) or pharmaceutically or cosmetically acceptable salt thereof. In certain embodiments, the pharmaceutical composition or cosmetic composition comprises 1.4-1.6 wt % of the compound of Formula (I) or pharmaceutically or cosmetically acceptable salt thereof. In some embodiments, the pharmaceutical composition or cosmetic composition comprises 1.6-1.8 wt % of the compound of Formula (I) or pharmaceutically or cosmetically acceptable salt thereof. In certain embodiments, the pharmaceutical composition or cosmetic composition comprises 1.8-2 wt % of the compound of Formula (I) or pharmaceutically or cosmetically acceptable salt thereof.

Additional Methods and Uses

The present disclosure also provides methods for making the compounds provided herein (e.g., compounds of Formula (I)), and pharmaceutically or cosmetically acceptable salts thereof.

Provided herein is a method for making a compound of Formula (I), or a pharmaceutically or cosmetically acceptable salt thereof, the method comprising:
a) Providing a solution of unmodified hyaluronic acid of Formula (Ia):

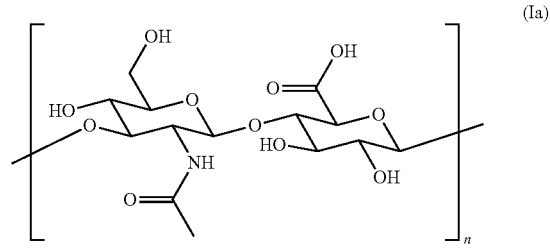

or a salt thereof, wherein n is an integer from 1-20,000;
b) Contacting the solution with a diaminoalkyl compound under suitable conditions to obtain amine-functionalized HA, or a salt thereof;
c) Reacting the amine-functionalized HA or salt thereof with a compound comprising a hydrophobic moiety, to obtain the compound of Formula (I), or pharmaceutically or cosmetically acceptable salt thereof.

In certain embodiments, the solution of step (a) is a buffered solution. In some embodiments, the solution of step (a) is a buffered solution of acidic pH. In certain embodiments, the solution of step (a) is a buffered solution of pH 3.0-7.0. In some embodiments, the solution of step (a) is a buffered solution of pH 4.0-6.0. In certain embodiments, the solution of step (a) is a buffered solution of pH 3.0-4.0. In some embodiments, the solution of step (a) is a buffered solution of pH 4.0-5.0. In certain embodiments, the solution of step (a) is a buffered solution of pH 5.0-6.0. In some embodiments, the solution of step (a) is a buffered solution of pH 6.0-7.0. In certain embodiments, the solution of step (a) is a buffered solution of pH 4.5. In some embodiments, the solution of step (a) is a buffered solution of pH 5.0. In certain embodiments, the solution of step (a) is a buffered solution of pH 5.5. In some embodiments, the solution of step (a) is an MES buffer. In certain embodiments, the solution of step (a) is an MES buffer of pH 5.0.

In certain embodiments, the solution of step (a) comprises at least 0.1 kg of unmodified hyaluronic acid of Formula (Ia). In some embodiments, the solution of step (a) comprises at least 0.5 kg of unmodified hyaluronic acid of Formula (Ia). In certain embodiments, the solution of step (a) comprises at least 1 kg of unmodified hyaluronic acid of Formula (Ia). In some embodiments, the solution of step (a)

comprises at least 2 kg of unmodified hyaluronic acid of Formula (Ia). In certain embodiments, the solution of step (a) comprises at least 5 kg of unmodified hyaluronic acid of Formula (Ia). In some embodiments, the solution of step (a) comprises at least 10 kg of unmodified hyaluronic acid of Formula (Ia).

In certain embodiments, the solution of (a) comprises at least 1% of unmodified hyaluronic acid of Formula (Ia) by weight. In some embodiments, the solution of (a) comprises at least 2% of unmodified hyaluronic acid of Formula (Ia) by weight. In certain embodiments, the solution of (a) comprises at least 5% of unmodified hyaluronic acid of Formula (Ia) by weight. In certain embodiments, the solution of (a) comprises at least 10% of unmodified hyaluronic acid of Formula (Ia) by weight. In some embodiments, the solution of (a) comprises at least 20% of unmodified hyaluronic acid of Formula (Ia) by weight.

In certain embodiments, the suitable conditions of step (b) comprise a temperature range of 0-30° C. In some embodiments, the suitable conditions of step (b) comprise a temperature range of 0-10° C. In certain embodiments, the suitable conditions of step (b) comprise a temperature range of 0-5° C. In some embodiments, the suitable conditions of step (b) comprise a temperature of 4° C.

In certain embodiments, the suitable conditions of step (b) comprise a reaction period of 1-72 hours. In some embodiments, the suitable conditions of step (b) comprise a reaction period of 1-48 hours. In certain embodiments, the suitable conditions of step (b) comprise a reaction period of 12-36 hours. In some embodiments, the suitable conditions of step (b) comprise a reaction period of 16-28 hours. In certain embodiments, the suitable conditions of step (b) comprise a reaction period of 24 hours.

In certain embodiments, the suitable conditions of step (b) comprise use of an activating agent or catalyst. In some embodiments, the activating agent is a carbodiimide, or a salt thereof. In certain embodiments, the activating agent is 1-ethyl-3-(3-dimethylaminopropyl)carbodiimide, N,N'-dicyclohexylcarbodiimide, or N,N'-diisopropylcarbodiimide, or a salt thereof. In some embodiments, the activating agent is N,N'-dicyclohexylcarbodiimide, or a salt thereof. In certain embodiments, the activating agent is N,N'-diisopropylcarbodiimide, or a salt thereof. In some embodiments, the activating agent is 1-ethyl-3-(3-dimethylaminopropyl)carbodiimide, or a salt thereof. In certain embodiments, the activating agent is the activating agent is the hydrochloride salt of 1-ethyl-3-(3-dimethylaminopropyl)carbodiimide (EDC-HCl).

In certain embodiments, the solution of unmodified hyaluronic acid of Formula (Ia), or a salt thereof, and the activating agent are reacted for an activation period prior to contacting the solution with the diaminoalkyl compound. In some embodiments, the activation period is about 0.1-5.0 hours. In certain embodiments, the activation period is about 0.5-2.0 hours. In some embodiments, the activation period is about 1.0 hours.

In certain embodiments, the diaminoalkyl compound is

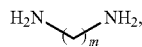

and m is 2-12. In some embodiments, the diaminoalkyl compound is

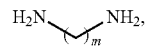

and m is 2, 3, 4, 5, 6, 7, 8, 9, 10, 11, or 12. In some embodiments, the diamino alkyl compound is

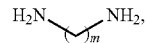

and m is 2-6. In certain embodiments, the diaminoalkyl compound is ethylenediamine. In some embodiments, the diaminoalkyl compound is 1,3-diaminopropane. In certain embodiments, the diaminoalkyl compound is 1,4-diaminobutane. In some embodiments, the diaminoalkyl compound is 1,5-diaminopentane. In certain embodiments, the diaminoalkyl compound is 1,6-diaminohexane.

In certain embodiments, step (b) achieves at least 1% functionalization. In some embodiments, step (b) achieves at least 5% functionalization. In certain embodiments, step (b) achieves at least 10% functionalization. In some embodiments, step (b) achieves 1-25% functionalization. In certain embodiments, step (b) achieves 1-5% functionalization. In some embodiments, step (b) achieves 5-10% functionalization. In certain embodiments, step (b) achieves 10-15% functionalization. In some embodiments, step (b) achieves 15-20% functionalization. In certain embodiments, step (b) achieves 20-25% functionalization.

In certain embodiments, the step of contacting the solution with a diaminoalkyl compound is performed to prevent an exotherm.

In certain embodiments, the amine-functionalized HA, or a salt thereof, is isolated prior to step (c). In certain embodiments, the amine-functionalized HA, or a salt thereof, is isolated by precipitation prior to step (c). In certain embodiments, the amine-functionalized HA, or a salt thereof, is purified prior to step (c). In certain embodiments, the amine-functionalized HA, or a salt thereof, is purified by precipitation prior to step (c). In some embodiments, the amine-functionalized HA, or a salt thereof, is isolated by precipitation into acetone. In certain embodiments, the amine-functionalized HA, or a salt thereof, is purified by precipitation into acetone.

In certain embodiments, step (c) is performed in a buffered solution. In some embodiments, the solution of step (c) is a buffered solution of basic pH. In certain embodiments, the buffered solution has a pH of 7.0-11.0. In some embodiments, the buffered solution has a pH of 7.0-9.0. In certain embodiments, the buffered solution has a pH of 7.0-8.0. In some embodiments, the buffered solution has a pH of 8.0-9.0. In certain embodiments, the buffered solution has a pH of 7.5. In some embodiments, the buffered solution has a pH of 8.0. In certain embodiments, the buffered solution is HEPES buffer. In some embodiments, the buffered solution is HEPES buffer of pH 7.5.

In certain embodiments, step (c) is performed at 15-60° C. In some embodiments, step (c) is performed at 30-50° C. In certain embodiments, step (c) is performed at 35-45° C. In some embodiments, step (c) is performed at 40° C.

In certain embodiments, reacting the amine-functionalized HA, or a salt thereof, with the compound comprising the hydrophobic moiety comprises stirring at a rate up to 300 RPM. In some embodiments, reacting the amine-functionalized HA, or a salt thereof, with the compound comprising the hydrophobic moiety comprises stirring at a rate up to 200

RPM. In certain embodiments, reacting the amine-functionalized HA, or a salt thereof, with the compound comprising the hydrophobic moiety comprises stirring at a rate up to 150 RPM. In some embodiments, reacting the amine-functionalized HA, or a salt thereof, with the compound comprising the hydrophobic moiety comprises stirring at a rate of 150 RPM.

In certain embodiments, the hydrophobic moiety has the formula —C(O)R$_3$, wherein R$_3$ is substituted or unsubstituted aliphatic. In certain embodiments, R$_3$ is C$_{8-35}$ aliphatic. In some embodiments, R$_3$ is C$_9$-C$_{19}$ aliphatic. In certain embodiments, R$_3$ is C$_{11}$ aliphatic. In some embodiments, R$_3$ is substituted or unsubstituted alkyl. In some embodiments, R$_3$ is substituted C$_{8-35}$ alkyl. In some embodiments, R$_3$ is substituted C$_9$-C$_{19}$ alkyl. In some embodiments, R$_3$ is unsubstituted C$_{8-35}$ alkyl. In some embodiments, R$_3$ is unsubstituted C$_9$-C$_{19}$ alkyl. In certain embodiments, R$_3$ is unsubstituted C$_9$ alkyl. In some embodiments, R$_3$ is unsubstituted C$_{10}$ alkyl. In certain embodiments, R$_3$ is unsubstituted C$_{11}$ alkyl. In some embodiments, R$_3$ is unsubstituted C$_{12}$ alkyl. In certain embodiments, R$_3$ is unsubstituted C$_{13}$ alkyl. In some embodiments, R$_3$ is unsubstituted C$_{14}$ alkyl. In certain embodiments, R$_3$ is unsubstituted Cis alkyl. In some embodiments, R$_3$ is unsubstituted C$_{16}$ alkyl. In certain embodiments, R$_3$ is unsubstituted C$_{17}$ alkyl. In some embodiments, R$_3$ is unsubstituted C$_{18}$ alkyl. In certain embodiments, R$_3$ is unsubstituted C$_{19}$ alkyl. In some embodiments, R$_3$ is substituted or unsubstituted alkenyl. In some embodiments, R$_3$ is substituted C$_{8-35}$ alkenyl. In some embodiments, R$_3$ is substituted C$_9$-C$_{19}$alkenyl. In some embodiments, R$_3$ is unsubstituted C$_{8-35}$ alkenyl. In some embodiments, R$_3$ is unsubstituted C$_9$-C$_{19}$ alkenyl. In certain embodiments, R$_3$ is unsubstituted C$_9$ alkenyl. In some embodiments, R$_3$ is unsubstituted C$_{10}$ alkenyl. In certain embodiments, R$_3$ is unsubstituted C$_{11}$ alkenyl. In some embodiments, R$_3$ is unsubstituted C$_{12}$ alkenyl. In certain embodiments, R$_3$ is unsubstituted C$_{13}$ alkenyl. In some embodiments, R$_3$ is unsubstituted C$_{14}$ alkenyl. In certain embodiments, R$_3$ is unsubstituted C$_{15}$ alkenyl. In some embodiments, R$_3$ is unsubstituted C$_{16}$ alkenyl. In certain embodiments, R$_3$ is unsubstituted C$_{17}$ alkenyl. In some embodiments, R$_3$ is unsubstituted C$_{18}$ alkenyl. In certain embodiments, R$_3$ is unsubstituted C$_{19}$ alkenyl.

In certain embodiments, the compound comprising the hydrophobic moiety further comprises an electrophilic moiety. In some embodiments, the compound comprising the hydrophobic moiety further comprises an NHS-ester, mixed anhydride, carbonic anhydride, activated ester, aryl halide, alkyl halide, alcohol, aldehyde, ketone, alkylborane, boronic acid, or boronic ester. In certain embodiments, the compound comprising the hydrophobic moiety further comprises an NHS-ester. In certain embodiments, the compound comprising the hydrophobic moiety is an N-hydroxysuccinimide (NHS)-functionalized fatty acid. In some embodiments, the compound comprising the hydrophobic moiety is an NHS-functionalized unsaturated fatty acid. In certain embodiments, the compound comprising the hydrophobic moiety is NHS-functionalized myristoleic acid, NHS-functionalized palmitoleic acid, NHS-functionalized sapienic acid, NHS-functionalized oleic acid, NHS-functionalized elaidic acid, NHS-functionalized vaccenic acid, NHS-functionalized linoleic acid, or NHS-functionalized linoelaidic acid. In some embodiments, the compound comprising the hydrophobic moiety is an NHS-functionalized saturated fatty acid. In certain embodiments, the compound comprising the hydrophobic moiety is NHS-functionalized caprylic acid, NHS-functionalized pelargonic acid, NHS-functionalized capric acid, NHS-functionalized undecylic acid, NHS-functionalized lauric acid, NHS-functionalized tridecylic acid, NHS-functionalized myristic acid, NHS-functionalized pentadecylic acid, NHS-functionalized palmitic acid, NHS-functionalized margaric acid, NHS-functionalized stearic acid, NHS-functionalized nondecylic acid, or NHS-functionalized arachidic acid. In some embodiments, the compound comprising the hydrophobic moiety is NHS-functionalized lauric acid. In certain embodiments, the compound comprising the hydrophobic moiety has the structure

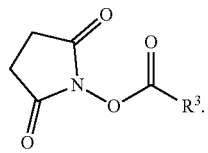

In some embodiments, the compound comprising the hydrophobic moiety has the structure

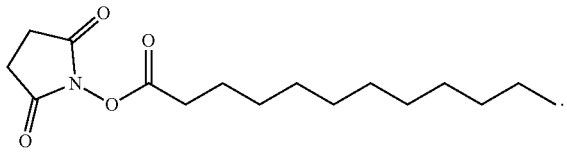 [SMILES: CCCCCCCCCCCC(=O)ON1C(=O)CCC1=O]

In certain embodiments, step (c) achieves greater than 50% functionalization. In some embodiments, step (c) achieves greater than 60% functionalization. In certain embodiments, step (c) achieves greater than 70% functionalization. In some embodiments, step (c) achieves greater than 80% functionalization. In certain embodiments, step (c) achieves greater than 85% functionalization. In some embodiments, step (c) achieves greater than 90% functionalization. In certain embodiments, step (c) achieves greater than 95% functionalization. In some embodiments, step (c) achieves greater than 98% functionalization.

In certain embodiments, one or more steps are performed in aqueous solvent. In some embodiments, one or more steps are performed in an organic solvent. In certain embodiments, one or more steps are performed in a polar protic solvent. In some embodiments, one or more steps are performed in water, methanol, ethanol, isopropyl alcohol, n-butanol or acetic acid. In certain embodiments, one or more steps are performed in a polar aprotic solvent. In some embodiments, one or more steps are performed in dichloromethane, tetrahydrofuran, ethyl acetate, acetonitrile, dimethylformamide, dimethyl sulfoxide, or acetone. In certain embodiments, one or more steps are performed in dimethylformamide. In certain embodiments, one or more steps are performed in a mixture of aqueous and organic solvents. In some embodiments, one or more steps are performed in a mixture of aqueous solvent and dimethylformamide. In certain embodiments, step (c) is performed in a mixture of aqueous solvent and dimethylformamide.

In certain embodiments of the method of synthesis, the compound of Formula (I) or pharmaceutically or cosmetically acceptable salt thereof is characterized as being substantially free of free amines. In some embodiments of the method of synthesis, free amines are unreacted diaminoalkyl compounds or unreacted amine-functionalized HA. In certain embodiments, free amines are unreacted diaminoalkyl compounds. In some embodiments of the method of synthesis, free amines are unreacted amine-functionalized HA. In certain embodiments of the method of synthesis, free amines comprise less than 10% of N-containing moieties present in the composition. In some embodiments of the method of synthesis, free amines comprise less than 5% of N-containing moieties present in the composition. In certain embodiments of the method of synthesis, free amines comprise less than 2% of N-containing moieties present in the composition. In some embodiments of the method of synthesis, free amines comprise less than 1% of N-containing moieties present in the composition. In certain embodiments of the method of synthesis, free amines comprise less than 0.5% of N-containing moieties present in the composition. In some embodiments of the method of synthesis, free amines comprise less than 0.1% of N-containing moieties present in the composition.

In certain embodiments of the method of synthesis, the compound of Formula (I) or pharmaceutically or cosmetically acceptable salt thereof is characterized as being substantially free of cross-linked hyaluronic acid. In some embodiments of the method of synthesis, the composition comprising a compound of Formula (I), or a pharmaceutically or cosmetically acceptable salt thereof, is characterized as comprising fewer than three cross-links per chain. In certain embodiments of the method of synthesis, the composition comprising a compound of Formula (I), or a pharmaceutically or cosmetically acceptable salt thereof, is characterized as comprising fewer than two cross-links per chain.

In certain embodiments, the unmodified hyaluronic acid of Formula (Ia) has the structure:

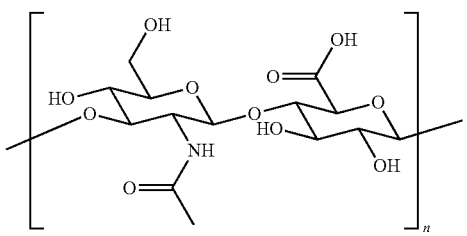

(Ia)

or a salt thereof, wherein n is an integer from 5-50.

In certain embodiments, the amine-functionalized HA is of Formula (Ib):

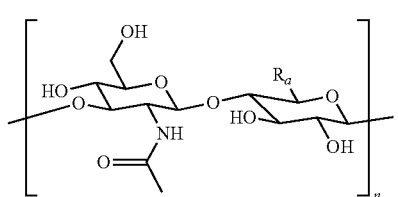

(Ib)

or a pharmaceutically or cosmetically acceptable salt thereof, wherein:

n is an integer from 5-50;

each $R_a$ is independently —$CO_2H$, or a group of Formula (III):

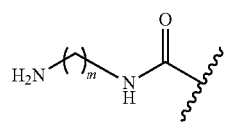

(III)

wherein m is 2-12; and provided that at least 1% of R groups comprise a group of Formula (III).

In certain embodiments, m is 2-12. In some embodiments, m is 2, 3, 4, 5, 6, 7, 8, 9, 10, 11, or 12. In certain embodiments, m is 2-6. In some embodiments, m is 2. In certain embodiments, m is 3. In some embodiments, m is 4. In certain embodiments, m is 5. In some embodiments, m is 6.

In certain embodiments, the compound of Formula (I) has the structure:

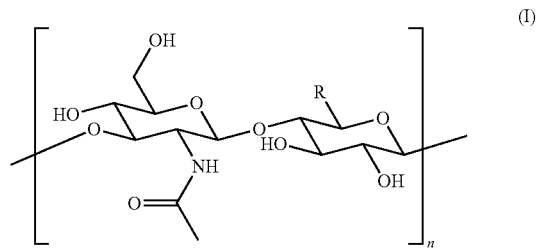

(I)

or a pharmaceutically or cosmetically acceptable salt thereof, wherein:

n is an integer from 1-20,000;

each R is independently —$CO_2H$, or a group of Formula (II):

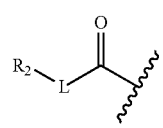

(II)

wherein L is

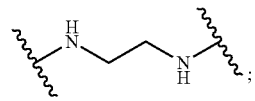 [SMILES: *NCCN*]

$R_2$ is a fatty acid residue of the formula —$C(O)R_3$, wherein $R_3$ is $C_{9-19}$ unsubstituted alkyl; and provided that at least 1% of R groups comprise a group of Formula (II).

In certain embodiments, the method for making a compound of Formula (I), or a pharmaceutically or cosmetically acceptable salt thereof, comprises:

a) Providing a solution of unmodified hyaluronic acid of Formula (Ia):

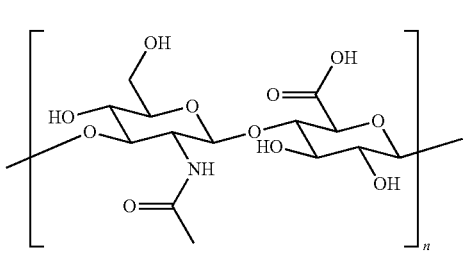
(Ia)

or a salt thereof, wherein n is an integer from 1-20,000;

b) Contacting the solution with a diaminoalkyl compound under suitable conditions to obtain a compound of Formula (Ib):

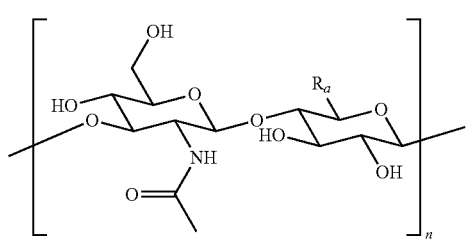
(Ib)

or a salt thereof, wherein n is an integer from 1-20,000;

each $R_a$ is independently —$CO_2H$, or a group of formula (III):

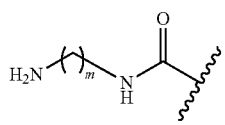
(III)

wherein m is 2-12; and provided that at least 1% of $R_a$ groups comprise a group of formula (III);

c) Reacting the amine-functionalized HA or salt thereof with a compound comprising a hydrophobic moiety having the structure

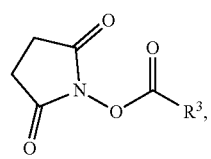

wherein $R_3$ is substituted or unsubstituted aliphatic, to obtain the compound of Formula (I), or a pharmaceutically or cosmetically acceptable salt thereof.

In certain embodiments, the method for making a compound of Formula (I) wherein n is 5-50, or a pharmaceutically or cosmetically acceptable salt thereof, comprises:

a) Providing a solution of unmodified hyaluronic acid of Formula (Ia):

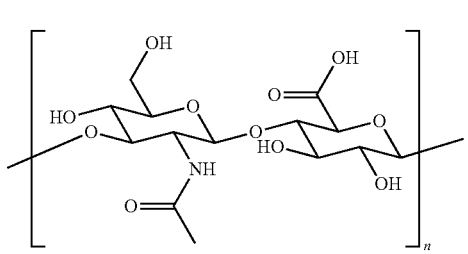
(Ia)

or a salt thereof, wherein n is an integer from 5-50;

b) Contacting the solution with a diaminoalkyl compound under suitable conditions to obtain a compound of Formula (Ib):

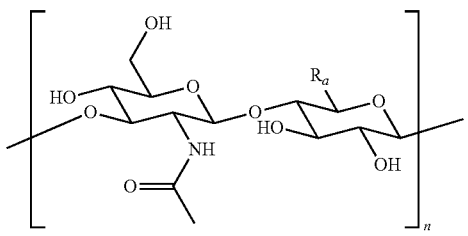
(Ib)

or a salt thereof, wherein n is an integer from 5-50;

each $R_a$ is independently —$CO_2H$, or a group of formula (III):

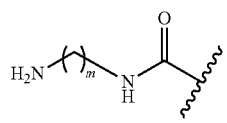
(III)

wherein m is 2-12; and provided that at least 1% of $R_a$ groups comprise a group of formula (III);

c) Reacting the amine-functionalized HA or salt thereof with a compound comprising a hydrophobic moiety having the structure

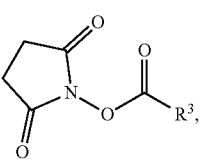

wherein $R_3$ is substituted or unsubstituted aliphatic, to obtain the compound of Formula (I) wherein n is 5-50, or a pharmaceutically or cosmetically acceptable salt thereof.

In certain embodiments, the method for making a compound of Formula (I) wherein n is 20-30, or a pharmaceutically or cosmetically acceptable salt thereof, comprises:

a) Providing a solution of unmodified hyaluronic acid of Formula (Ia):

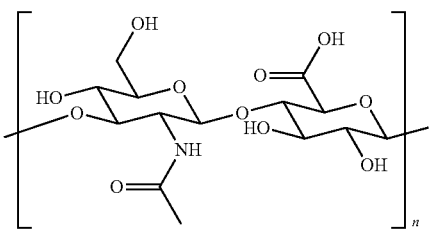

(Ia)

or a salt thereof, wherein n is an integer from 20-30;
b) Contacting the solution with a diaminoalkyl compound under suitable conditions to obtain a compound of Formula (Ib):

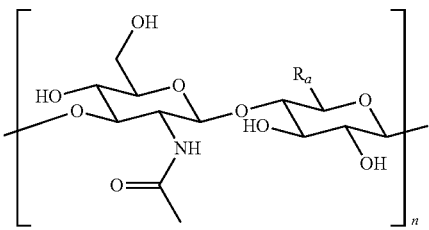

(Ib)

or a salt thereof, wherein n is an integer from 20-30;
each $R_a$ is independently —$CO_2H$, or a group of formula (III):

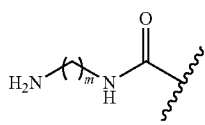

(III)

wherein m is 2-12; and
provided that at least 1% of $R_a$ groups comprise a group of formula (III);
c) Reacting the amine-functionalized HA or salt thereof with a compound comprising a hydrophobic moiety having the structure

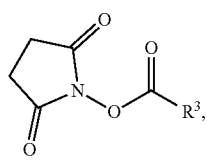

wherein $R_3$ is substituted or unsubstituted aliphatic, to obtain the compound of Formula (I) wherein n is 20-30, or a pharmaceutically or cosmetically acceptable salt thereof.

Examples

Herein, a scalable method is demonstrated for high volume hyaluronic acid-lipid (HA-lipid) bioconjugation to produce a variant of HA that has stronger physical association with the skin, increasing retention time. This bioconjugation was carried out at a 1 kg scale to demonstrate scale-up production at a high concentration of 10% w/v. First, HA is functionalized with ethylenediamine in aqueous conditions to introduce a reactive linker, targeting 5-10% of functionalized amine for lipid modification. Amine-modified HA was precipitated in acetone, and free ethylenediamine was removed. Second, N-hydroxysuccinimide (NHS)-lipid is grafted to the amine-functionalized HA. This reaction was carried out in aqueous buffer due to the high solubility of HA, decreased production cost, and decreased environmental impact compared to using organic solvents. The final product, HA-lipid, was purified by precipitation with acetone. The final grafting density of lipid on HA was 8.5%, and neither free amines nor cross-linked HA were detected. Lipid-grafted HA was evaluated for cell cytotoxicity and immunogenicity, and skin penetration and testing were performed using porcine skin. The modified HA-lipid proved to be non-immunogenic and non-cytotoxic, as shown via IL-6 production and MTT assay cell viability assays in fibroblasts. The HA-lipid showed a significantly higher skin penetration and longer restoration, up to 24 hours, than unmodified HA.

The major challenge in HA and lipid bioconjugation is identifying conditions where both reagents are soluble and where the reaction is scalable, meaning that the reaction can be performed under concentrated conditions without the use of costly solubilizing agents. Highly charged HA is predominantly soluble in aqueous solvents, while lipids are most soluble in organic solvents. Several reports have shown compatibilization of the two reagents using agents such as PEG, but the lower concentration of HA in the reaction and large concentration of PEG required limits the use of the reagent on industrial scale.[7,32,37] To meet these criteria, a synthetic scheme was designed that could be performed in water with high reactant concentration, as illustrated in FIG. 1. Prior to lipid modification, lauric acid was chosen as the lipid moiety. This long length fatty acid (16 carbons) has been reported to enhance skin penetration and binding affinity to cell membranes compared to short chain (<$C_6$) and medium-chain ($C_6$-$C_8$) fatty acid.[39] Lauric acid is readily available and cost efficient starting material that can be easily used to synthesize bioconjugates. For conjugation on amine modified HA, N-hydroxysuccimide (NHS) ester-based chemistry was used to modify primary amine is selective, effective and fast, leading to formation of a stable amide bond between the primary amine and NHS.[40,41] Since this reaction occurs under mild condition at pH 7.0-9.0, this reaction is preferable in water/organic co-solvent system.[42] Here, lauric acid was functionalized with N-hydroxysuccinimide to form lauric-NHS ester (lauric-NHS) as shown in FIG. 1A. The formation of purified lauric-NHS (LA-NHS) was verified by $^1H$ NMR and $^{13}C$ NMR.

The reaction was performed at the 1 kg scale in a 15 L reactor, effectively demonstrating scale-up. Following synthesis, purification can be easily accomplished at scale via precipitation of the amine-functionalized HA ($HA-NH_2$) in acetone and water (1:2 (v/v)). There are two distinct peaks of ethyl group in 1H NMR from EDA were confirmed the HA modification with $NH_2$. Although EDC coupling for amine conjugation can cause self-crosslinking of a single polymer chain, none was observed even at the relatively high concentrations used in this synthesis. Compared to the unmodified HA retention time (22.3 mins, $M_w$: 1.07×104 g/mol) on gel permeation chromatography, $HA-NH_2$ showed a small shift in retention time (22.6 mins, $M_w$: 1.55×104 g/mol), showing no significant change in molecular weight after modification with amine in FIG. 2A indicating no crosslinking during the reaction. The small increase in molecular weight of HA-NH$_2$ may be due to the amine functionalization.

Figure 2A:
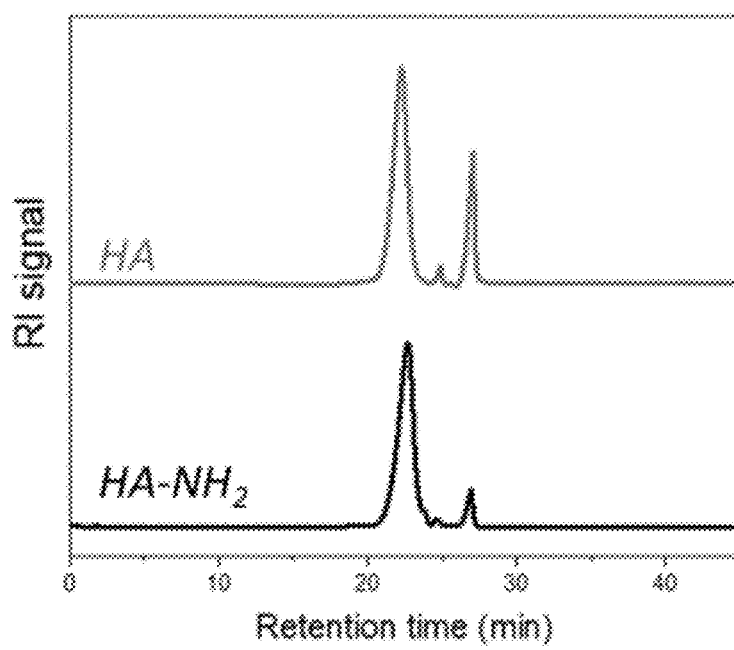
FIG. 2A shows GPC trace of HA and HA-NH2.
Figure 2B:
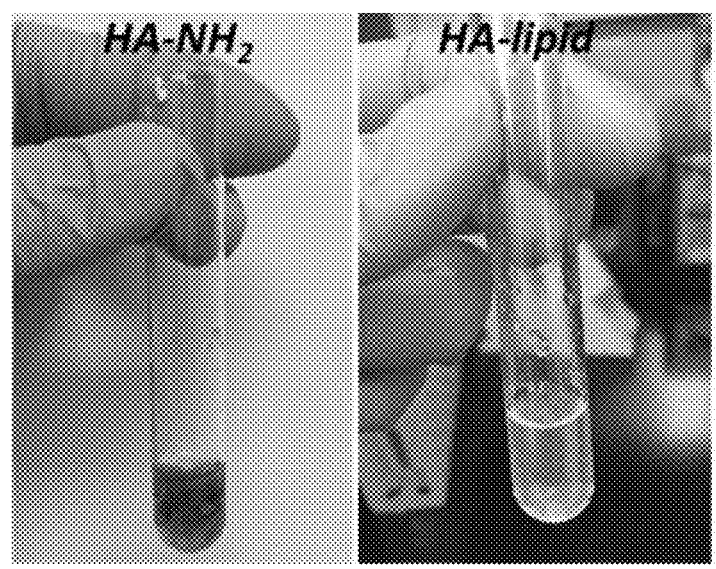
FIG. 2B shows an image indicating ninhydrin test of $HA-NH_2$ and HA-lipid.
Figure 2C:
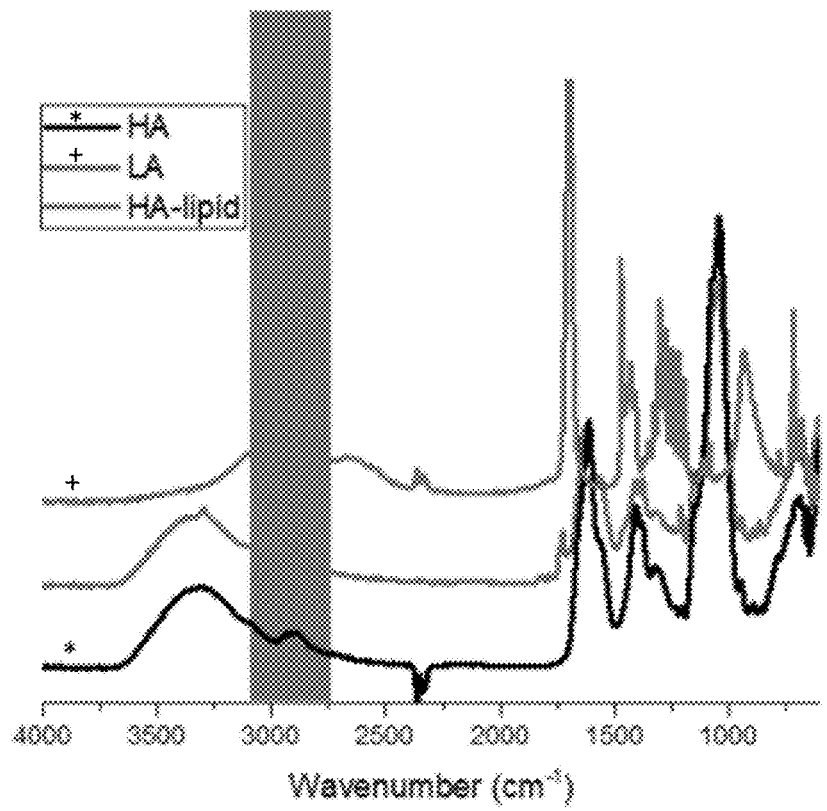
FIG. 2C shows FTIR ATR spectra showing aliphatic $CH_2$ and $CH_3$ signals from lipid and lipid conjugated HA, but there is no shown aliphatic C—H signal in HA.
Figure 3A:
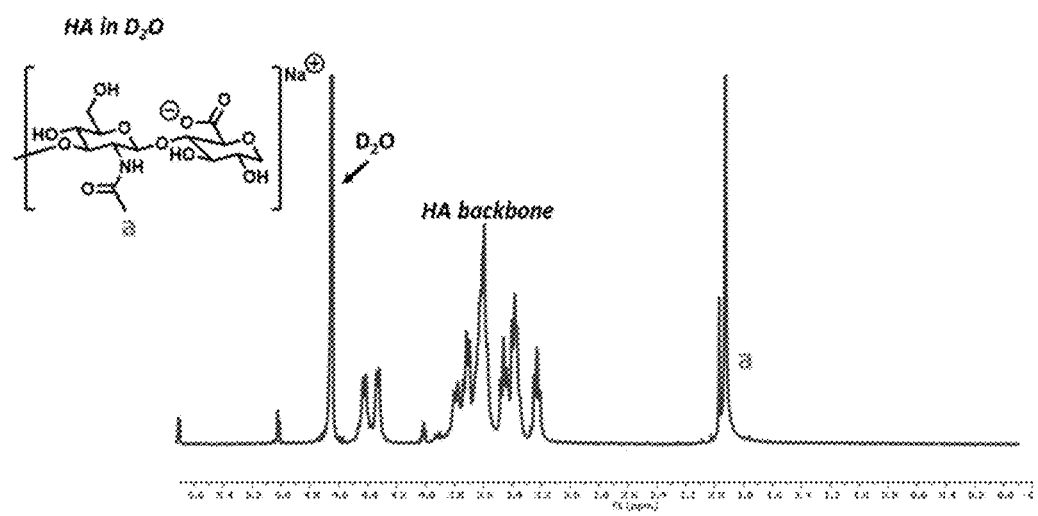
FIGS. 3A-3B show $^1H$ NMR spectra.

Subsequently, HA-NH$_2$ and lauric-NHS were conjugated in HEPES buffer at pH 7.0 in the pilot-scale chemical reactor. Performing the reaction in aqueous buffer rather than organic solvents has offered many advantages. First, HA is highly soluble in water, and the lauric-NHS can be added to the reaction as a solution in DMF. The reaction mixture is homogenous following gentle heating to 40° C. as an optically clear mixture solution, since the set temperature is the melting temperature of lauric acid. Conjugation in aqueous buffer also allows for the reduced use of organic solvents, providing for easy clean up and purification procedures. To confirm the modification products as well as purification efficiency, the ninhydrin test was used because it is a fast and sensitive method after purification of the reaction with precipitation of HA-lipid with acetone and water (1:2 (v/v)). The ninhydrin test confirmed the amine modification of HA with ethylene diamine. When reacted with the HA-NH$_2$, the ninhydrin test indicated the presence of primary amines from HA-NH$_2$ while HA-lipid gives a negative result in FIG. 2B. This indicates the lack of free amines in HA-lipid. FTIR ATR spectroscope was used to investigate the grafting of lauric acid in HA-NH$_2$. After grafting lauric acid, HA-lipid show the two peaks corresponding to the CH$_2$ and CH$_3$ from the lipid. FIG. 2C shows C—H stretching vibration of alkane from lauric-NHS show 2916 cm$^{-1}$ and 2848 cm$^{-1}$. $^1$H NMR was utilized for characterization of the modified molecules. The peak assignment of ethylene functionality shows from 2.78 to 2.71 ppm, confirmed the successful conjugation of ethylene diamine while $^1$H NMR spectrum of HA does not show any signal at the same ppm in FIG. 3A. The proton from the lipid indicate at 1.17 ppm and 0.79 ppm that corresponded to the assigned peak of NHS-lauric acid. One notable point is, since the solubility of lipid modified HA in water is poor due to the grafted hydrophobic lipids, deuterated (CD$_3$)$_2$SO$_4$ was used as the NMR solvent while unmodified HA was dissolved in D$_2$O.

Figure 3B:
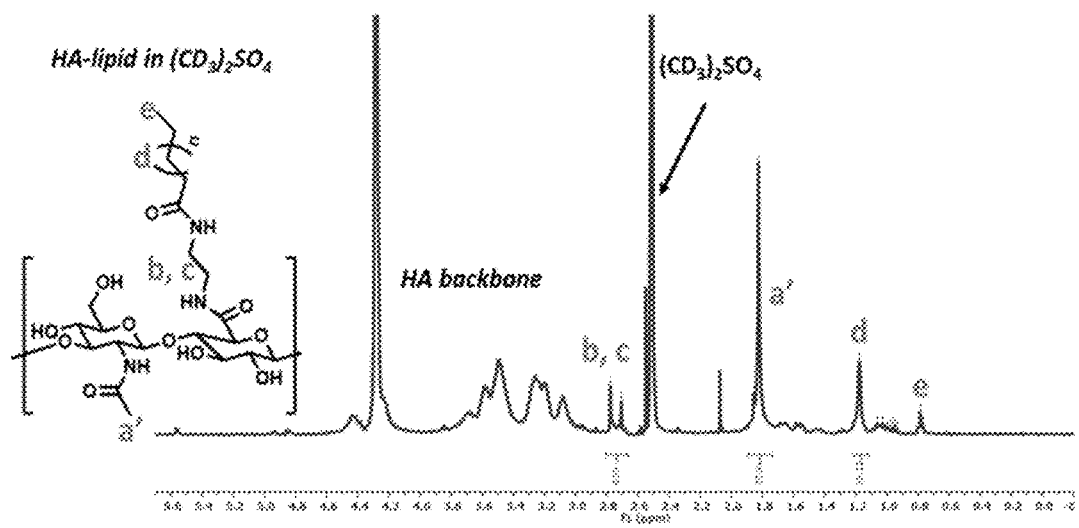

Because of that, there are slightly shifted peaks such as methyl peak between HA and HA-lipid. The lipid grafting density from HA-NH$_2$ was calculated via NMR integration indicating approximately 2.1 repeat units modified with lipid to HA that has 25 monomer repeat units. Therefore, the functionalization reaction yielded 8.5% amine functionalization and 100% lipid modification showing that the extra lipid was completely removed by purification. The NMR data supports the 8.5% modification with lipid because of the corresponding peak areas in FIG. 3B. This result indicates the successful conjugation of lauric acid to the primary amines of HA, as well as successful purification with no amount of starting material that has free amine in the final product. This is important especially in cosmetic applications since the toxic effects of free amine moieties are skin irritants when it contacts dermatitis human skin.[43]

Figure 4A:
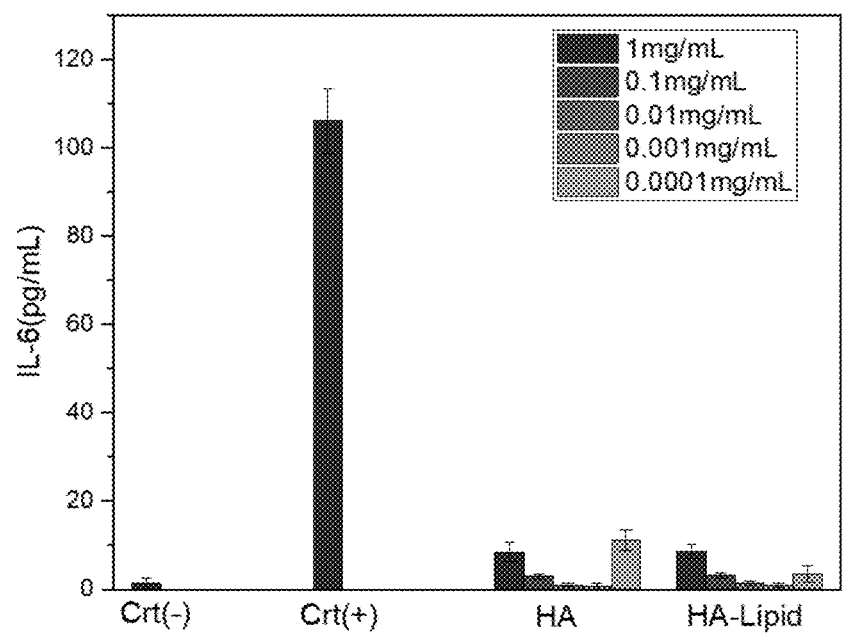
FIG. 4A shows the effect of various concentrations of HA and HA-lipid (24 hr, 37° C.) on NIH 3T3 cells measured by IL-6 production. The key showing data at concentrations of 1 mg/mL to 0.0001 mg/mL is represented left to right, respectively, on the graph for the following conditions: Crt(−), Crt(+), HA, and HA-Lipid.

Cytotoxicity and inflammation were assessed to provide a measure of the biocompatibility of the HA-lauric acid bioconjugate for use in cosmetic or biomedical products. HA is used in cosmetic applications at concentrations up to 1%.[44] Therefore, in vitro experiments were carried out with a maximum of 1% HA or HA-lipid. First, to determine the immunogenicity of HA-lipid, the production of inflammatory cytokine IL-6 from NIH 3T3 fibroblasts was measured following 24-hours of incubation. This is because IL-6 is involved with inflammation and infection responses and in the regulation of metabolic, regenerative, and neural processes.[45] NIH 3T3 cells produced minimal levels of IL-6, under 10 pg/mL, after HA treatment of the fibroblasts (FIG. 4A). HA-lipid was also found to be non-immunogenic, with comparable amounts of IL-6 produced to that of HA.

Figure 4B:
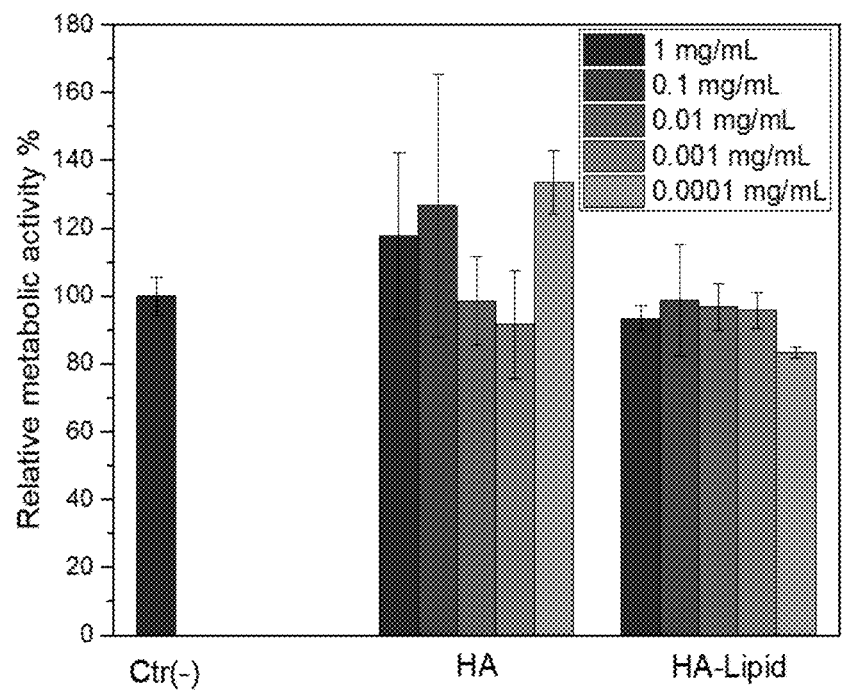
FIG. 4B shows the effect of various concentrations of HA and HA-lipid (24 hr, 37° C.) on NIH 3T3 cells, measured by cytotoxicity. The key showing data at concentrations of 1 mg/mL to 0.0001 mg/mL is represented left to right, respectively, on the graph for the following conditions: Crt(−), HA, and HA-Lipid.

Further, to assess the cytotoxicity of modified HA, cell metabolic activity was measured using MTT test. NIH3T3 fibroblasts were incubated with HA, and HA-lipid at varying concentrations (0.0001 to 1 mg/mL) for 24 hrs. No significant changes in cell viability were found in a various concentration of both HA and HA-lipid. The NIH3T3 fibroblasts showed no significant reduction in viability after treatment with HA or with the modified HA-lipid compared to the control with only cell media (FIG. 4B).

Figure 5:
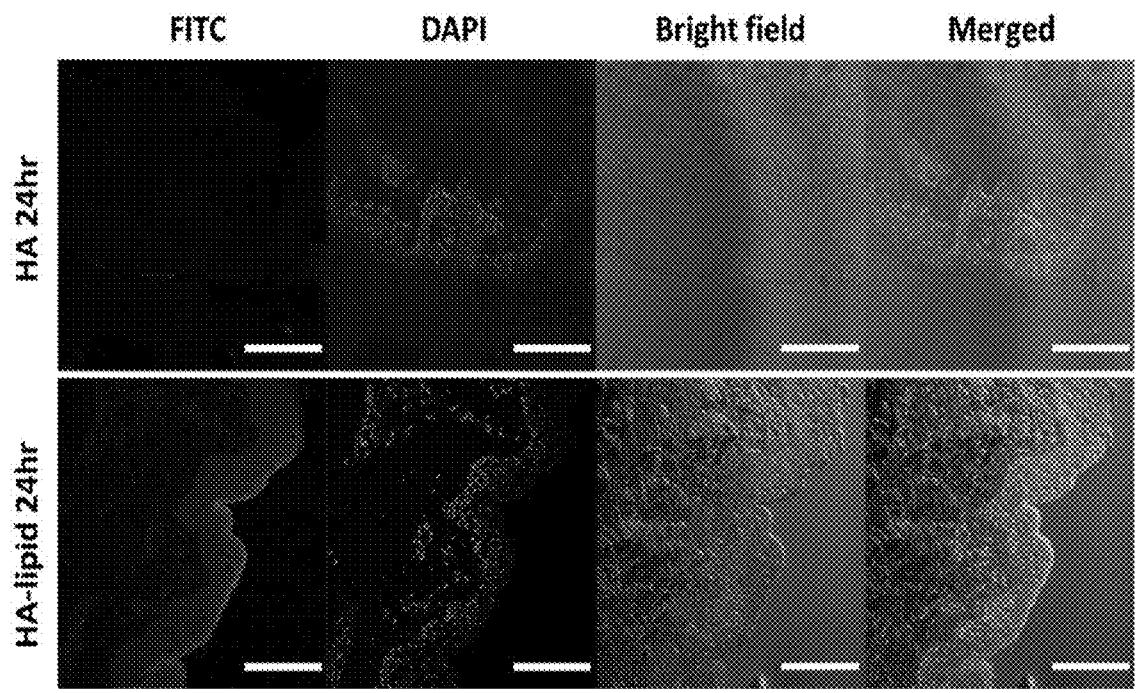
FIG. 5 shows a skin penetration test of FITC labeled HA and HA-lipid into porcine skin after 24 hrs adding with the donor solution (HA-FITC and HA-lipid-FITC each), porcine skin was visualized by confocal laser scanning microscopy (CLSM). FITC, Dapi, bright field and merged images of FITC-labeled HA and FITC-labeled HA-lipid each. Scale bar is 100 μm.

To evaluate the efficacy of the skin permeation and retention enhancement, the penetration of fluorescently labeled HA and HA-lipid into porcine skin was analyzed. FITC conjugated short chain HA (FITC-HA) was used as a control to easily compare the skin permeation degree of the FITC labeled lipid modified HA (HA-lipid-FITC) by fluorescence. An ex vivo skin permeation study of FITC-labeled HA variants was performed using porcine skin and confocal laser scanning microscopy (CLSM) images. After 24 hour of application, HA-FITC was only observed on the outer most layer of the epidermis and did not permeate into the stratum corneum (FIG. 5). In contrast, HA-lipid-FITC was observed with enhanced fluorescence signal in both epidermis layers and the stratum corneum, and in the dermis through diffusion from the stratum corneum to the dermis. This also shows the ability of HA-lipid to stay retained in the skin for 24 hrs. Previous reports have shown low retention properties of HA of under the course of the day.[3,4,6] Contrary to previous reports, HA after functionalized with lipid remains after the skin for 24 hrs.

The results reported herein demonstrate a scalable path for the synthesis of HA-lipid bioconjugates in aqueous based solvent, creating product at the kg scale. The chemical characterization confirmed approximately 9% grafted lipid in HA. Interestingly, in various concentrations, modified HA-lipid has shown no cytotoxic or immunogenic activity in NIH 3T3 fibroblast cells. Moreover, modified HA-lipid showed enhanced skin penetration and retention in porcine skin compared to unmodified HA. Hence, the finding that HA-lipid as the improved skin penetration system can be directly delivered into the skin without hassles that can be a potential candidate in pharmaceutical and cosmetic application.

Synthesis and Characterization

Materials

Hyaluronic acid (~10 kDa) was obtained from Elizabeth Arden (Revlon). N-Hydroxysuccinimide (NHS), fluorescein isothiocyanate (FITC), Trimethylamine (TEA), N,N'-Dicyclohexylcarbodiimide (DCC), lauric acid (LA), 1-ethyl-3-[3-dimethylaminopropyl]carbodiimide (EDC), ethylenediamine (EDA) were purchased from Sigma-Aldrich. Acetone and DMF were purchased from ThermoFisher Scientific. Aqueous solutions were prepared with Milli-Q water from a Millipore system (>18 MΩcm). IL-6 ELISA Kits were purchased from MiliporeSigma. Dulbecco's Modified Eagle Medium (DMEM), penicillin, streptomycin, trypsin, phosphate buffered saline (PBS), fetal bovine serum (FBS), and Vybrant MTT cell proliferation assay were purchased from ThermoFisher Scientific. NIH 3T3 cells were purchased from ATCC. Porcine skin was purchased from a local butcher shop.

Instrumentation

All NMR spectral data were obtained using a Bruker AVANCE-400 NMR spectrometer with a Magnex Scientific superconducting magnet. UV-Vis spectra were recorded on a Varian Cary 50 Bio UV/visible spectrophotometer. Fourier Transform Infrared Attenuated Total Reflectance (FTIR-ATR) spectroscopy was conducted on a Digilab FTS 7000 spectrometer. A confocal laser scanning microscope was conducted on ZEISS CLSM 700.

Synthesis of LA-NHS

N-hydroxy succinamide (NHS; 3.45 g, 30 mmol), lauric acid (6 g, 30 mmol), and N,N'-Dicyclohexylcarbodiimide (DCC) (6.18 g, 30 mmol) were added to 150 mL of dried ethyl acetate at room temperature and stirred overnight. White byproduct, dicyclohexyl urea, was filtered off. The ethyl acetate solution was concentrated and then recrystallized in ethyl alcohol. After cooling down to room temperature, the final product formed white shiny powder (yield 90%). $^1$H NMR (CDCl$_3$, 400 MHz): δ 2.85 (s, —OC(CH$_2$)$_2$CO—), 2.62 (t, —C$\underline{H_2}$CO—) 1.76 (m, —CH$_2$C$\underline{H_2}$CH$_2$—) 1.42-1.28 (m, —C$\underline{H_2}$CH$_2$—), 0.9 (t, CH$_3$). $^{13}$C NMR (CDCl$_3$, 400 MHz): δ 169.2 (—OC-NCO—), 168.7 (—COO—) 25.6 (OC($\underline{C}$H$_2$)$_2$CO), 14.1 ($\underline{C}$H$_3$)

Ethylene Diamine Functionalization of HA 1 kg of HA was dissolved in 10 L of MES buffer (0.1 M, pH 5.0) and mixed in the 15 L reactor. The reactor temperature was set up at room temperature. After completely dissolving HA in the buffer, EDC·HCl (>97.0%, 100.4 g) was added with stirring 150 RPM at 4° C. For activation of EDC·HCl, the mixture of HA was stirred for 1 hour, and then ethylenediamine (EDA, 26.3 mL) was added dropwise. The reaction proceeded for 24 hours. Amine-functionalized HA was precipitated in 20 L of acetone, and the white powder (HA-EDA) was collected and dried in vacuum oven. The obtained yield was 80%.

$^1$H NMR (D$_2$O, 400 MHz): δ 2.81 (m, —CH$_2$C$\underline{H_2}$NH$_2$—), 3.29 (m, —C$\underline{H_2}$CH$_2$NH$_2$), 1.95 (s, C$\underline{H_3}$—C=O—)

Bioconjugation of HA and Lipid

HA-EDA (0.8 kg) was dissolved in HEPES buffer (pH 7.5, 9 L). 156 g NHS-functionalized LA was dissolved in DMF (1 L). NHS-LA solution in DMF was added to the HA solution in the reactor and stirred at 150 RPM. The reaction temperature was increased to 40° C. to dissolve LA-NHS in the reaction solution completely, yielding a clear mixture. After 24 hours, the crude solution was purified by precipitation of HA in acetone. White powder was obtained and dried in vaccuo. $^1$H NMR confirmed lipid modification and the grafting density and ninhydrin test was utilized to investigate no residual free amine left in the final product. The obtained yield of the final material was 68%.

$^1$H NMR ((CD3)$_2$SO$_4$, 400 MHz): δ 2.78 (—C$\underline{H_2}$—CH$_2$—NH$_2$), 2.71 (—CH$_2$—C$\underline{H_2}$—NH$_2$), 1.83 (C$\underline{H_3}$—C=O—), 1.18 (—CH$_2$—($\underline{C}$H$_2$)$_n$—CH$_2$—), 0.79 (—(CH$_2$)$_n$—CH$_2$—C$\underline{H_3}$)

Synthesis of FITC-Labeled HA-Lipid

Figure 6:
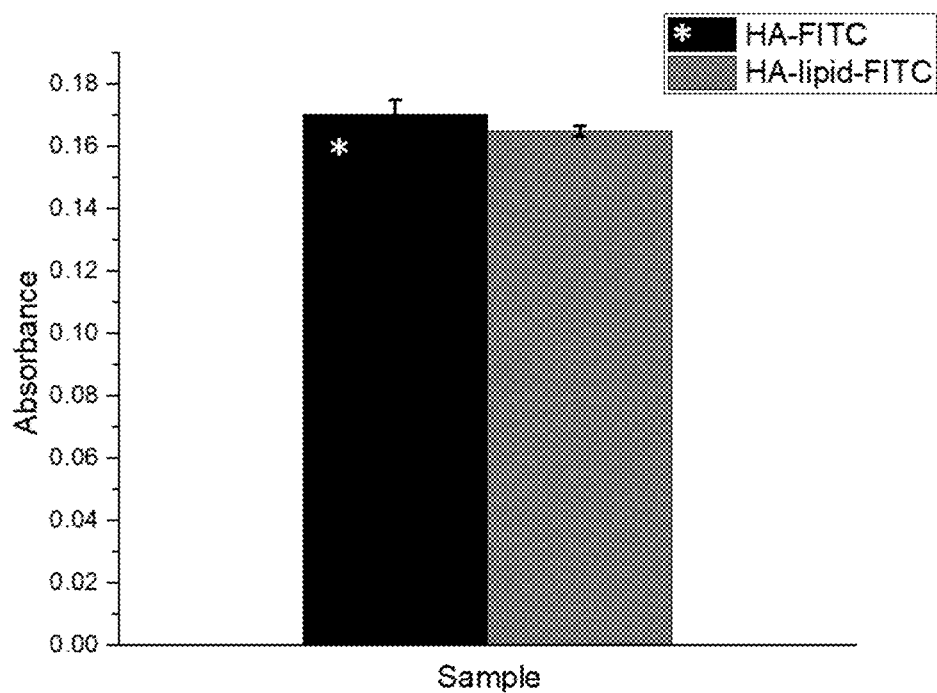
FIG. 6 shows UV absorbance of FITC-labeled HA and FITC-labeled HA-lipid.

Fluorescein isothiocyanate (FITC; 11 mg, 30 mmol) was dissolved in 3 mL of anhydrous DMSO. 2.6 g of HA-lipid (2.6 g, 0.26 mmol) was dissolved in 100 mL of deionized water. Triethylamine (4.1 mg, 30 mmol) was added into the HA solution and then stirred for 1 hour. The FITC in DMSO was slowly added to the mixture of HA-lipid solution. The reaction was stirred at room temperature for 16 hours. The crude solution was dialyzed against 4.5 L of Milli-Q water. The water was changed 7 times with fresh water, once every 3 hours, until free FITC was not observed in the dialyzed water. The purified FITC labeled HA-lipid was lyophilized. The FITC modified HA is light yellow color. The FITC modification was not detectable by NMR, however, FITC modified HA and HA-lipid at the same concentration (3 mg/mL) showed a similar absorbance intensity at 495 nm (FIG. 6). Using the molar extinction coefficient (c) for FITC, 73,000 cm$^{-1}$M$^{-1}$, the concentration of FITC in the HA and HA-lipid solution were 2.33×10$^{-6}$ mM and 2.26×10$^{-6}$ mM respectively.

Confirmation of Ethylenediamine and Lipid Conjugation with Ninhydrin Assay

To confirm the existence of free amine after modification with lipid, ninhydrin assay was utilized. 20 mg of the final product (HA-lipid) was dissolved in 2 mL of the mixture (DMSO: water, 1:1 (v/v)) and placed in the test tube. 0.2 g ninhydrin, 0.5 mL acetic acid and 100 mL n-Butanol and 4.5 mL water were mixed thoroughly for preparation of ninhydrin solution. 200 μL ninhydrin solution was added in the test tube. HA-lipid solution and ninhydrin solution was mixed by gently shaking the mixture solution. The test tube was heated until the mixture solution boils for 10 sec. The color of the solution was investigated by observing. For the control, HA conjugated with ethylenediamine was tested with ninhydrin solution to confirm the existence primary amine by showing strong purple color.

Cell Cytotoxicity and Immunogenicity Assays

Cell Culture

NIH3T3 fibroblast cells were cultured in Dulbecco's Modified Eagle Medium (DMEM) with 10% premium fetal bovine serum and 1%© penicillin-streptomycin. Cells were incubated in 75 cm$^2$ cell culture flasks at 37° C., in a 95% air and 5% CO$_2$ environment. At 80-90% confluency, the cells were detached with trypsin for 5 minutes at 37° C. The detached cells were collected by centrifugation at 800 g for 5 minutes. 1×10$^4$ cells were placed per well in a 96-well culture plate and cultured for 24 hours. After 24 hours, various concentration of HA and HA-lipid were added into each well (n=3) and incubated for 24 hours.

In Vitro Cytotoxicity Assay

NIH 3T3 fibroblast cells were plated in 96 well plates at 10,000 cells/well. Varying concentrations of HA and HA-lipid were added from 1 mg/mL to 1×10$^{-4}$ mg/mL. Untreated cells served as negative controls. Treatment with lipopolysaccharide was used as a positive control. The cells were then incubated at 37° C. with 5% CO$_2$ for 16 hours. The cell media was removed and 10 μL MTT solution (5 mg/mL) in DMEM was added into each well and incubated for 4 hours at 37° C., which reduces a yellow tetrazolium salt (3-(4,5-dimethylthiazol-2-yl)-2,5-diphenyltetrazolium bromide, MTT) to formazan, an insoluble crystalline product with a deep purple color. The medium was then carefully aspirated, and remaining formazan crystals were dissolved 100 μL of DMSO. The 96-well plate was placed on a shaker to completely redisolve the crystal into the solvent. Finally, the absorbance was determined at 570 nm by a plate reader.

$$\text{Cell viability (\%)} = \frac{\text{Absorbance (polymer)}}{\text{Absorbance (control)}} \times 100 \qquad (1)$$

In Vitro Immunogenicity Assay

The potential inflammatory activity of HA and HA-lipid was evaluated by measuring IL-6 production. NIH 3T3 fibroblast cells were plated in 96 well plates at 10,000 cells/well. Varying concentrations of HA and HA-lipid were added from 1 mg/mL to 1×10$^4$ mg/mL. Untreated cells served as negative controls. Treatment with lipopolysaccharide was used as a positive control. The cells were then incubated at 37° C. with 5% CO$_2$ for 16 hours. The cell media (50 μL) was transferred to antibody-coated ELISA plates which were read following the supplied protocol from the manufacturer (BioLegend, Mouse IL-6 ELISA MAX™ Set (Deluxe)).

Skin Penetration and Retention Assays

Ex Vivo Tests of Penetration and Retention

Penetration studies were performed with full thickness porcine skin. Porcine skin was selected as a model because of histologically similarities with human skin and a comparable SC thickness.[36] First, frozen porcine skin was cut into 5 mm by 5 mm squares and thawed in PBS for 2 hours. The stratum corneum was stripped by applying and removing adhesive tape 30 times. Various concentrations of HA and HA-lipid labeled with FITC were prepared in PBS solution (pH 7.4). Each skin sample was placed in a mesh well insert. The bottom of the well was filled with 1 mL of PBS to keep the skin hydrated. The insert was placed in 100 mmol solution of FITC labeled HA and HA-lipid. 10 μL of each test solution was applied to the top of each skin sample. The treated skin was maintained at 37° C. for 24 hr. Following incubation, the porcine skin was washed with PBS. The skin samples were subsequently frozen in OCT freezing medium. The frozen skin samples were sectioned at 10 μm thickness. The cryo-sectioned tissue sections were stained with DAPI and mounted with Prolong Glass mounting buffer (ThermoFisher). The mounted sections were observed using a confocal laser scanning microscope (ZEISS CLSM 700).

REFERENCES (1) Ganceviciene, R.; Liakou, A. I.; Theodoridis, A.; Makrantonaki, E.; Zouboulis, C. C. Skin Anti-Aging Strategies. *Dermatoendocrinol.* 2012, 4 (3), 308-319. doi.org/10.4161/derm.22804.

(2) Farage, M. A.; Miller, K. W.; Elsner, P.; Maibach, H. I. Characteristics of the Aging Skin. *Adv. Wound Care* 2013, 2 (1), 5-10. doi.org/10.1089/wound.2011.0356.

(3) Papakonstantinou, E.; Roth, M.; Karakiulakis, G. Hyaluronic Acid: A Key Molecule in Skin Aging. *Dermatoendocrinol.* 2012, 4 (3), 253-258. doi.org/10.4161/derm.21923.

(4) Boer, M.; Duchnik, E.; Maleszka, R.; Marchlewicz, M. Structural and Biophysical Characteristics of Human Skin in Maintaining Proper Epidermal Barrier Function. *Adv. Dermatol. Allergol. Dermatol. Alergol.* 2016, 33 (1), 1-5. doi.org/10.5114/pdia.2015.48037.

(5) Fallacara, A.; Baldini, E.; Manfredini, S.; Vertuani, S. Hyaluronic Acid in the Third Millennium. *Polymers* 2018, 10 (7), 701. doi.org/10.3390/polym10070701.

(6) Schiraldi, C.; Gatta, A. L.; Rosa, M. D. Biotechnological Production and Application of Hyaluronan. *Biopolymers* 2010. doi.org/10.5772/10271.

(7) Tokudome, Y.; Komi, T.; Omata, A.; Sekita, M. A New Strategy for the Passive Skin Delivery of Nanoparticulate, High Molecular Weight Hyaluronic Acid Prepared by a Polyion Complex Method. *Sci. Rep.* 2018, 8 (1), 2336. doi.org/10.1038/s41598-018-20805-3.

(8) Baumann, L. Skin Ageing and Its Treatment. *J. Pathol.* 2007, 211 (2), 241-251. doi.org/10.1002/path.2098.

(9) Litwiniuk, M.; Krejner, A.; Speyrer, M. S.; Gauto, A. R.; Grzela, T. Hyaluronic Acid in Inflammation and Tissue Regeneration. *Wounds Compend. Clin. Res. Pract.* 2016, 28 (3), 78-88.

(10) Noble, P. W.; Liang, J.; Jiang, D. Hyaluronan as an Immune Regulator in Human Diseases. *Physiol. Rev.* 2011, 91 (1), 221-264. doi.org/10.1152/physrev.00052.2009.

(11) Longinotti, C. The Use of Hyaluronic Acid Based Dressings to Treat Burns: A Review. *Burns Trauma* 2014, 2 (4), 162. doi.org/10.4103/2321-3868.142398.

(12) Chiummariello, S.; Arleo, S.; Alfano, C. [Aminoacids and hyaluronic acid in topical treatment of bedsores. Clinical report]. *Il G. Chir.* 2010, 31 (5), 251-255.

(13) Yıldırım, S.; Özener, H. Ö.; Doğan, B.; Kuru, B. Effect of Topically-Applied Hyaluronic-Acid on Pain and Palatal Epithelial Wound Healing: An Examiner-Blind, Randomized, Controlled Clinical Trial. *J. Periodontol.* 2017, 1-14. doi.org/10.1902/jop.2017.170105.

(14) Dereure, O.; Czubek, M.; Combemale, P. Efficacy and Safety of Hyaluronic Acid in Treatment of Leg Ulcers: A Double-Blind RCT. *J. Wound Care* 2012, 21 (3), 131-139. doi.org/10.12968/jowc.2012.21.3.131.

(15) Kong, M.; Chen, X. G.; Kweon, D. K.; Park, H. J. Investigations on Skin Permeation of Hyaluronic Acid Based Nanoemulsion as Transdermal Carrier. *Carbohydr. Polym.* 2011, 86 (2), 837-843. doi.org/10.1016/j.carbpol.2011.05.027.

(16) Sano, K.; Gotoh, M.; Dodo, K.; Tajima, N.; Shimizu, Y.; Murakami-Murofushi, K. Age-Related Changes in Cyclic Phosphatidic Acid-Induced Hyaluronic Acid Synthesis in Human Fibroblasts. *Hum. Cell* 2018, 31 (1), 72-77. doi.org/10.1007/s13577-017-0185-7.

(17) Baran, R.; Maibach, H. *Textbook of Cosmetic Dermatology*; CRC Press, 2010.

(18) Design of Novel BSA/Hyaluronic Acid Nanodispersions for Transdermal Pharma Purposes—Molecular Pharmaceutics (ACS Publications) pubs.acs.org/doi/full/10.1021/mp400657 g?src=recsys (accessed Jul. 13, 2018).

(19) Brown, M. B.; Jones, S. A. Hyaluronic Acid: A Unique Topical Vehicle for the Localized Delivery of Drugs to the Skin. *J. Eur. Acad. Dermatol. Venereol.* 2005, 19 (3), 308-318. doi.org/10.1111/j.1468-3083.2004.01180.x.

(20) Essendoubi, M.; Gobinet, C.; Reynaud, R.; Angiboust, J. F.; Manfait, M.; Piot, O. Human Skin Penetration of Hyaluronic Acid of Different Molecular Weights as Probed by Raman Spectroscopy. *Skin Res. Technol. Off. J. Int. Soc. Bioeng. Skin ISBS Int. Soc. Digit. Imaging Skin ISDIS Int. Soc. Skin Imaging ISSI* 2016, 22 (1), 55-62. doi.org/10.1111/srt.12228.

(21) Kuehl, C.; Zhang, T.; Kaminskas, L. M.; Porter, C. J. H.; Davies, N. M.; Forrest, L.; Berkland, C. Hyaluronic Acid Molecular Weight Determines Lung Clearance and Biodistribution after Instillation. *Mol. Pharm.* 2016, 13 (6), 1904-1914. doi.org/10.1021/acs.molpharmaceut.6b00069.

(22) Zaikov, G. E. *Analysis and Performance of Engineering Materials: Key Research and Development*; CRC Press, 2015.

(23) Berlin, A. A.; Joswik, R.; Vatin, N. I. *The Chemistry and Physics of Engineering Materials: Limitations, Properties, and Models*; CRC Press, 2018.

(24) Andrews, S.; Lee, J. W.; Prausnitz, M. Recovery of Skin Barrier After Stratum Corneum Removal by Microdermabrasion. *AAPS PharmSciTech* 2011, 12 (4), 1393-1400. doi.org/10.1208/s12249-011-9715-x.

(25) Pappas, A. Epidermal Surface Lipids. *Dermatoendocrinol.* 2009, 1 (2), 72-76.

(26) Lin, T.-K.; Zhong, L.; Santiago, J. L. Anti-Inflammatory and Skin Barrier Repair Effects of Topical Application of Some Plant Oils. *Int. J. Mol. Sci.* 2017, 19 (1). doi.org/10.3390/ijms19010070.

(27) Lopes, L. B. Overcoming the Cutaneous Barrier with Microemulsions. *Pharmaceutics* 2014, 6 (1), 52-77. doi.org/10.3390/pharmaceutics6010052.

(28) Nolan, K.; Marmur, E. Moisturizers: Reality and the Skin Benefits. *Dermatol. Ther.* 2012, 25 (3), 229-233. doi.org/10.1111/j.1529-8019.2012.01504.x.

(29) Menegatti, S.; Zakrewsky, M.; Kumar, S.; Oliveira, J. S. D.; Muraski, J. A.; Mitragotri, S. De Novo Design of Skin-Penetrating Peptides for Enhanced Transdermal Delivery of Peptide Drugs. *Adv. Healthc. Mater.* 2016, 5 (5), 602-609. doi.org/10.1002/adhm.201500634.

(30) Williams, A. C.; Barry, B. W. Penetration Enhancers. *Adv. Drug Deliv. Rev.* 2004, 56 (5), 603-618. doi.org/10.1016/j.addr.2003.10.025.

(31) Vasovic, L. V.; Reich-Slotky, R.; Goel, R. Chapter 13—Hematopoietic Stem Cell Collections and Cellular Therapies. In *Clinical Principles of Transfusion Medicine*; Maitta, R. W., Ed.; Elsevier, 2018; pp 151-167. doi.org/10.1016/B978-0-323-54458-0.00013-1.

(32) Lee, H.; Lee, K.; Park, T. G. Hyaluronic Acid—Paclitaxel Conjugate Micelles: Synthesis, Characterization, and Antitumor Activity. *Bioconjug. Chem.* 2008, 19 (6), 1319-1325. doi.org/10.1021/bc8000485.

(33) McKay, C. S.; Finn, M. G. Click Chemistry in Complex Mixtures: Bioorthogonal Bioconjugation. *Chem. Biol.* 2014, 21 (9), 1075-1101. doi.org/10.1016/j.chembiol.2014.09.002.

(34) Hermanson, G. T. Chapter 24—Bioconjugation in the Study of Protein Interactions. In *Bioconjugate Techniques (Third Edition)*; Hermanson, G. T., Ed.; Academic Press: Boston, 2013; pp 989-1016. doi.org/10.1016/B978-0-12-382239-0.00024-8.

(35) Capello, C.; Fischer, U.; Hungerbühler, K. What Is a Green Solvent? A Comprehensive Framework for the Environmental Assessment of Solvents. *Green Chem.* 2007, 9 (9), 927-934. doi.org/10.1039/B617536H.

(36) Abd, E.; Yousef, S. A.; Pastore, M. N.; Telaprolu, K.; Mohammed, Y. H.; Namjoshi, S.; Grice, J. E.; Roberts, M. S. Skin Models for the Testing of Transdermal Drugs. *Clin. Pharmacol. Adv. Appl.* 2016, 8, 163-176. doi.org/10.2147/CPAA.S64788.

(37) Temperature- and pH-Controlled Hydrogelation of Poly (ethylene glycol)-Grafted Hyaluronic Acid by Inclusion Complexation with α-Cyclodextrin I Polymer Journal www.nature.com/articles/pj200446 (accessed Feb. 14, 2019).

(38) Dunetz, J. R.; Magano, J.; Weisenburger, G. A. Large-Scale Applications of Amide Coupling Reagents for the Synthesis of Pharmaceuticals. *Org. Process Res. Dev.* 2016, 20 (2), 140-177. doi.org/10.1021/op500305s.

(39) Kim, M.-J.; Doh, H.-J.; Choi, M.-K.; Chung, S.-J.; Shim, C.-K.; Kim, D.-D.; Kim, J. S.; Yong, C.-S.; Choi, H.-G. Skin Permeation Enhancement of Diclofenac by Fatty Acids. *Drug Deliv.* 2008, 15 (6), 373-379. doi.org/10.1080/10717540802006898.

(40) Nanda, J. S.; Lorsch, J. R. Chapter Eight—Labeling a Protein with Fluorophores Using NHS Ester Derivitization. In *Methods in Enzymology*; Lorsch, J., Ed.; Laboratory Methods in Enzymology: Protein Part A; Academic Press, 2014; Vol. 536, pp 87-94. doi.org/10.1016/B978-0-12-420070-8.00008-8.

(41) Stephanopoulos, N.; Francis, M. B. Choosing an Effective Protein Bioconjugation Strategy. *Nat. Chem. Biol.* 2011, 7 (12), 876-884. doi.org/10.1038/nchembio.720.

(42) Koniev, O.; Wagner, A. Developments and Recent Advancements in the Field of Endogenous Amino Acid Selective Bond Forming Reactions for Bioconjugation. *Chem Soc Rev* 2015, 44 (15), 5495-5551. doi.org/10.1039/C5CS00048C.

(43) Raoux, M.; Colomban, C.; Delmas, P.; Crest, M. The Amine-Containing Cutaneous Irritant Heptylamine Inhibits the Volume-Regulated Anion Channel and Mobilizes Intracellular Calcium in Normal Human Epidermal Keratinocytes. *Mol. Pharmacol.* 2007, 71 (6), 1685-1694. doi.org/10.1124/mol.106.033324.

(44) Becker, L. C.; Bergfeld, W. F.; Belsito, D. V.; Klaassen, C. D.; Marks, J. G.; Shank, R. C.; Slaga, T. J.; Snyder, P. W.; Cosmetic Ingredient Review Expert Panel; Andersen, F. A. Final Report of the Safety Assessment of Hyaluronic Acid, Potassium Hyaluronate, and Sodium Hyaluronate. *Int. J. Toxicol.* 2009, 28 (4 Suppl), 5-67. doi.org/10.1177/1091581809337738.

(45) Scheller, J.; Chalaris, A.; Schmidt-Arras, D.; Rose-John, S. The Pro- and Anti-Inflammatory Properties of the Cytokine Interleukin-6. *Biochim. Biophys. Acta* BBA—*Mol. Cell Res.* 2011, 1813 (5), 878-888. doi.org/10.1016/j.bbamcr.2011.01.034.

(46) Mero, A.; Campisi, M. Hyaluronic Acid Bioconjugates for the Delivery of Bioactive Molecules. *Polymers* 2014, 6 (2), 346-369. doi.org/10.3390/polym6020346.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

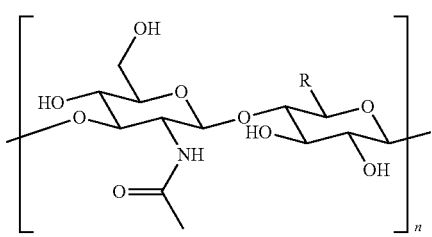

or a pharmaceutically or cosmetically acceptable salt thereof, wherein:
n is an integer from 1-20,000;
each R is independently —$CO_2H$, or a group comprising a hydrophobic moiety;
provided that at least 1% of R groups comprise a hydrophobic moiety; wherein the group comprising a hydrophobic moiety is of Formula (II):

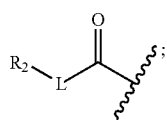

wherein each L is independently selected from the group consisting of:

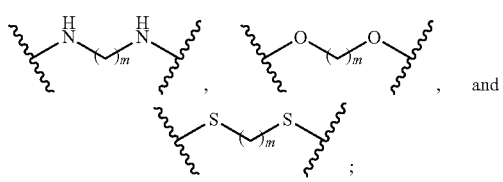

and
m is 2-12; and
each $R_2$ is independently a fatty acid residue of the formula —$C(O)R_3$, wherein each $R_3$ is $C_{8-35}$ aliphatic.

2. The compound or pharmaceutically or cosmetically acceptable salt of claim 1, wherein L is 1,2-diaminoethyl.

3. The compound or pharmaceutically or cosmetically acceptable salt of claim 1, wherein $R_3$ is $C_{11}$ aliphatic.

4. The compound or pharmaceutically or cosmetically acceptable salt of claim 1, wherein $R_3$ is $C_{8-35}$ alkyl.

5. The compound or pharmaceutically or cosmetically acceptable salt of claim 1, wherein n is 5-50.

6. The compound or pharmaceutically or cosmetically acceptable salt of claim 1, wherein at least 5% of R groups are of Formula (II).

7. The compound of Formula (I), having the structure:

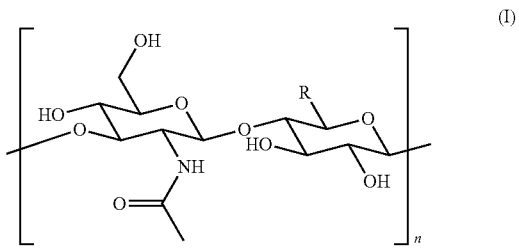

or a pharmaceutically or cosmetically acceptable salt thereof, of claim 1, wherein:
n is an integer from 5-50;
each R is independently —$CO_2H$, or a group of Formula (II):

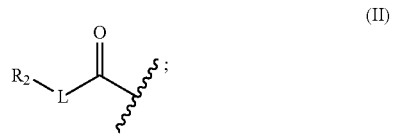

wherein L is

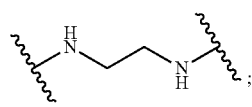 [SMILES: *NCCN*]

and
$R_2$ is a fatty acid residue of the formula —$C(O)R_3$, wherein $R_3$ is $C_{9-19}$ unsubstituted alkyl;
provided that at least 1% of R groups comprise a group of Formula (II).

8. The compound of Formula (I), having the structure:

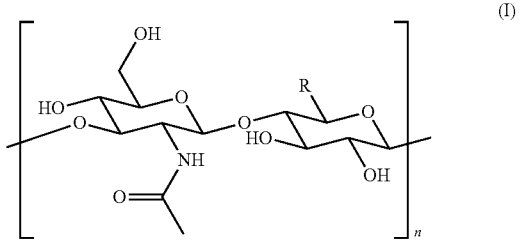

or a pharmaceutically or cosmetically acceptable salt thereof, of claim 1, wherein:
n is an integer from 5-50;
each R is independently —$CO_2H$, or a group of Formula (II):

(II)

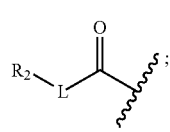

wherein L is

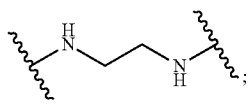 [SMILES: *NCCN*]

and
$R_2$ is a fatty acid residue of the formula —$C(O)R_3$, wherein $R_3$ is $C_{11}$ unsubstituted alkyl;
provided that at least 1% of R groups comprise a group of Formula (II).

9. The compound or pharmaceutically or cosmetically acceptable salt of claim 1, characterized as having increased skin penetration and/or increased skin retention relative to unmodified hyaluronic acid of Formula Ga1:

(Ia)

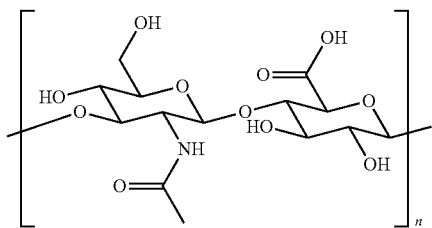

or a salt thereof, wherein n is an integer from 1-20,000.

10. The compound or pharmaceutically or cosmetically acceptable salt of claim 9, wherein the skin penetration and/or skin retention is increased for at least 12 hours.

11. A composition comprising an effective amount of the compound or pharmaceutically or cosmetically acceptable salt of claim 1, and optionally a pharmaceutically acceptable carrier or excipient.

12. A method for making the compound of Formula (I) according to claim 1, or a pharmaceutically or cosmetically acceptable salt thereof, wherein the group comprising a hydrophobic moiety is of Formula (II):

(II)

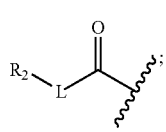

wherein L is

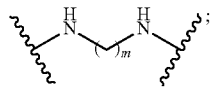

m is 2-12;
each $R_2$ is independently a fatty acid residue of the formula —$C(O)R_3$, and
each $R_3$ is $C_{8-35}$ aliphatic;
the method comprising:
a) Providing a solution of unmodified hyaluronic acid (HA) of Formula (Ia):

(Ia)

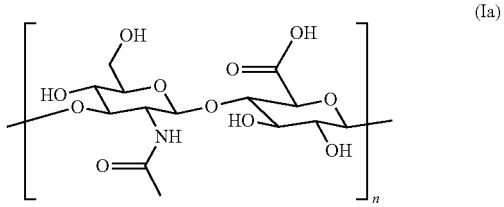

or a salt thereof, wherein n is an integer from 1-20,000;
b) Contacting the solution with a diaminoalkyl compound under suitable conditions to obtain amine-functionalized HA, or a salt thereof;
c) Reacting the amine-functionalized HA or salt thereof with the compound of Formula (II) comprising —C(O)$R_3$, to obtain the compound of Formula (I), or pharmaceutically or cosmetically acceptable salt thereof.

13. A kit comprising the compound of claim 1, or a pharmaceutically or cosmetically acceptable salt thereof; and
instructions for using the compound, pharmaceutically or cosmetically acceptable salt thereof, or pharmaceutical or cosmetic composition thereof.

* * * * *

UNITED STATES PATENT AND TRADEMARK OFFICE
CERTIFICATE OF CORRECTION

| | | |
|---|---|---|
| PATENT NO. | : 11,939,408 B2 | Page 1 of 1 |
| APPLICATION NO. | : 17/126700 | |
| DATED | : March 26, 2024 | |
| INVENTOR(S) | : Bradley David Olsen et al. | |

It is certified that error appears in the above-identified patent and that said Letters Patent is hereby corrected as shown below:

In the Claims

In Claim 9, at Column 81, Line 25, the text "Formula Gal" should be replaced with: --Formula (Ia)--.

Signed and Sealed this
Eighteenth Day of June, 2024

Katherine Kelly Vidal
*Director of the United States Patent and Trademark Office*